US006759189B1

(12) United States Patent
Meikle et al.

(10) Patent No.: US 6,759,189 B1
(45) Date of Patent: Jul. 6, 2004

(54) EARLY DETECTION OF LYSOSOMAL STORAGE DISORDERS

(75) Inventors: Peter J Meikle, Banksia Park (AU); Douglas A Brooks, North Cheltenham (AU); John J Hopwood, Stonyfell (AU)

(73) Assignee: Women's and Children's Hopital, North Adelaide (AU)

( * ) Notice: Subject to any disclaimer, the term of this patent is extended or adjusted under 35 U.S.C. 154(b) by 0 days.

(21) Appl. No.: 09/180,657

(22) PCT Filed: May 16, 1997

(86) PCT No.: PCT/AU97/00304

§ 371 (c)(1),
(2), (4) Date: Nov. 12, 1998

(87) PCT Pub. No.: WO97/44668

PCT Pub. Date: Nov. 27, 1997

(30) Foreign Application Priority Data

May 17, 1996 (AU) ............................................. PN 9917

(51) Int. Cl.$^7$ ................................................. C12Q 1/00
(52) U.S. Cl. ............................ 435/4; 435/7.1; 435/7.4; 435/7.7; 435/7.72; 435/7.9; 435/7.92
(58) Field of Search .............................. 435/4, 7.1, 7.4, 435/7.7, 7.71, 7.72, 7.9, 7.92, 183

(56) References Cited

U.S. PATENT DOCUMENTS 5,501,957 A    3/1996   Dennis et al.

FOREIGN PATENT DOCUMENTS

AU           29906/92       10/1993

OTHER PUBLICATIONS

Aerts et al. Eur. J. Biochem., vol. 150: 565–574, 1985.*
Colman et al. Research in Immunology. vol. 145: 33–36, 1994.*
Michelakakis et al. J. Inherit metab dis, vol: 18, p609–615, (Abstract Supplied), 1995.*
Alexander, Denis, et al; Five Related Lebanese Individuals with High Plasma Lysosomal Hydrolases: A New Defect in Mannose–6–Phosphate Receptor Recognition?; *American Journal of Human Genetics*; 1984; pp. 1001–1014; vol. 36, No. 5.
Brooks, D.A., et al.; Immunoquantifications of the Low Abundance Lysosomal Enzyme N–Acetylgalactosamine 4–Sulphatase; *Journal of Inherited Metabolic Disease*; 1990; pp. 108–120; vol. 13, No. 1.
Gatti, R., et al. Conparative Study of 15 Lysosomal Enzymes in Chorionic Villi and Cultured Amniotic Fluid Cells. Early prenatal diagnosis in seven pregnancies at risk for lysosomal storage diseases; *Prenatal Diagnosis*; Sep. 1985; pp. 329–336; vol. 5, No. 5.

Griffiths, Penelope A., et al.; Plasma Acid Hydrolases in Normal Adults and Children, and in Patients with some Lysosomal Storage Diseases; *International Journal of Clinical Chemistry*; Dec. 1, 1978; pp. 129–141; vol. 90, No. 2.
Guo, Yufeng, et al; Elevated plasma Chitotriosidase activity in various lysosomal storage disorders; *Journal of Inherited Metabolic Disease*; 1995; pp. 717–722; vol. 18, No. 6.
Kleiman, Frida, E., et al.; Sandhoff disease in Argentina: high frequency of a splice site mutation in the HEXB gene and correlation between enzyme and DNA–based tests for heterozygote detection; *Human Genetics*; 1994; pp. 279–282; vol. 94.
Lovell, Kathryn L., et al.; Biochemical and Histochemical Analysis of Lysosomal Enzyme Activities in Caprine β–Mannosidosis; *Molecular and Chemical Neuropathology*; 1994; pp. 61–74; vol. 21, No. 1.
McCabe, Norah R., et al.; Preferential Inhibition of Lysosomal Beta–Mannosidase by Sucrose; *Enzyme*; 1990; pp. 137–145; vol. 43, No. 3.
O'Brien, John S., et al.; Saposin proteins: structure, function, and role in human lysosomal storage disorders; *FASEB J.*; 1991; pp. 301–308; vol. 5.
Prence Elizabeth M., et al.; Diagnosis of α–Mannosidosis by measuring α–Mannosidase in Plasma; *Clinical Chemistry*; 1992; pp. 501–503; vol. 38, No. 4.
Whitley, Chester B., et al.; Long–Term Outcome of Hurler Syndrome Following Bone Marrow Transplantation; *American Journal of Medical Genetics*; Apr. 15, 1993; pp. 209–218; vol. 46, No. 2.
Yamaguchi, Keiko; Improvement of Tear Lysosomal Enzyme Levels after Treatment with Bone Marrow Transplantation in a Patient with I–Cell Disease; *Opthalmic Research*; 1989; pp. 226–229; vol. 21, No. 3.
Baghdiguian, S. et al.; Co–localization of suramin and serum albumin in lysosomes of suramin–treated human colon cancer cells; Cancer Letters; 1996; pp. 179–184; vol. 101.
Burkhardt, Janis K., et al.; The Giant Organelles in Beige and Chediak–Higashi Fibroblast Are Derived from Late Endosomes and Mature Lysosomes; Journal of Experimental Medicine; Dec. 1993; pp. 1845–1856; vol. 178.
Chamberlain, Paul, et al.; Generation and Characterization of Monoclonal Antibodies to Human Type–5 Tartrate–R-esistant Acid Phosphates: Development of a Specific Immunoassay of the Serum; Clinical Chemistry; 1995; pp. 1495–1499; vol. 41, No. 10.

(List continued on next page.)

*Primary Examiner*—Patrick J. Nolan
(74) *Attorney, Agent, or Firm*—Townsend and Townsend and Crew LLP

(57) ABSTRACT

The present invention relates generally to lysosomal storage disorders and to diagnostic agents for their detection in humans and other animals. More particularly, the present invention is directed to the uses of the LSD markers Lamp-1, Lamp-2, Limp-II, 4-sulphatase, acid phosphatase (ACP), β-hexosaminidase or α-mannosidase, amongst others as diagnostic agents for the detection of many lysosomal storage disorders.

28 Claims, 12 Drawing Sheets

OTHER PUBLICATIONS

Figure 1:
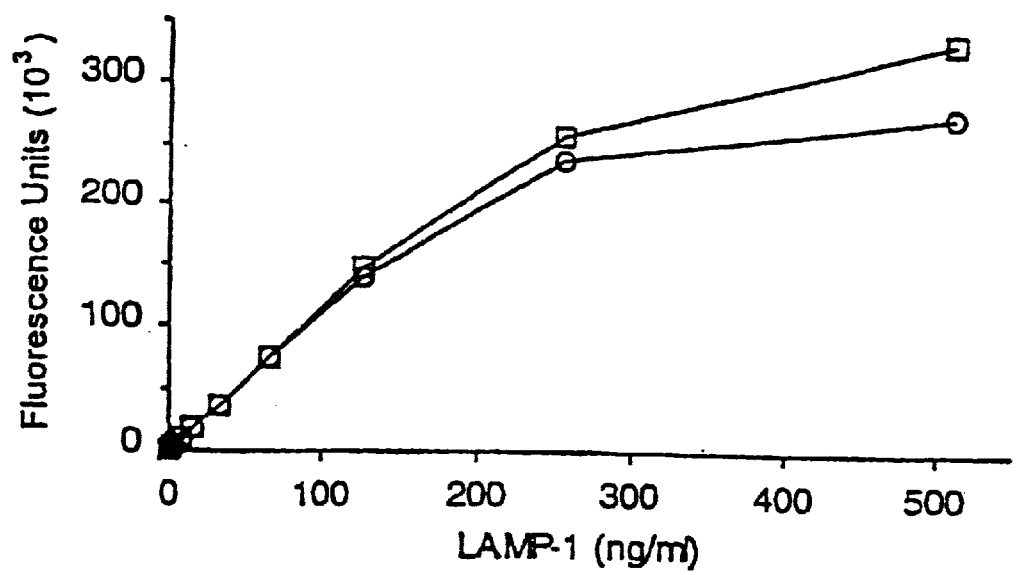

Conary, Jon T., et al.; Synthesis and Stability of Steroid Sulfatase in Fibroblasts from Multiple Sulfatase Deficiency; Biological Chemistry Hoppe–Seyler; Apr. 1988; pp. 297–302; vol. 369.

Dahlgren, Claes, et al.; The lysosomal membrane glycoproteins Lamp–1 and Lamp–2 are present in mobilizable organelles, but are absent from the azurophil granules of human neutrophils; Biochemical Journal; 1995; pp. 667–674; vol. 311.

Karageorgos, Litsa E. et al.; Lysosomal Biogenesis in Lysosomal Storage Disorders; Experimental Cell Research; 1997; pp. 85–97; vol. 234.

Kishimoto, Yasuo et al; Saposins: structure, function, distribution, and molecular genetics; Journal of Lipid Research; 1992; pp. 1255–1267; vol. 33.

Meikle, Peter J., et al.; Diagnosis of Lysosomal storage disorders: evaluation of lysosome–associated membrane protein LAMP–1 as diagnostic marker; Clinical Chemistry; 1997; pp. 1325–1335; vol. 43, No. 8.

Paschke, E. et al.; Infantile type of sialic acid storage disease with sialuria; Clinical Genetics; 1986; pp. 417–424; vol. 29.

Renlund, Martin, M.D.; Clinical and laboratory diagnosis of Salla disease in infancy and childhood; The Journal of Pediatrics; 1984; pp. 232–236; vol.104, No. 2.

Rendlund, Martin, et al.; Increased Urinary Excretion of Free N–Acetylneuraminic Acid in Thirteen Patients with Salla Disease; European Journal of Biochemistry; 1979; pp. 245–250; vol. 101.

Renlund, Martin, M.D., et al.; Salla disease: A new lysosomal storage disorder with disturbed sialic acid metabolism; Neurology; Jan. 1983; pp. 57–66; vol. 33.

Renlund, Martin, et al.; Studies on the Defect Underlying the Lysosomal Storage of Sialic Acid in Salia Disease: Lysosomal Accumulation of Sialic Acid Formed From N–Acetyl–Mannosamine or Derived from Low Density Lipoprotein in Cultured Mutant Fibroblasts; Journal of Clinical Investigation; Feb. 1986; pp. 568–574; vol. 77.

Rodriguez–Serna, Mercedes, Ph.D., et al. Angiokeratoma Corporis Diffusum Associated With β–Mannosidase Deficiency; Archives of Dermatology; Oct. 1996; pp. 1219–1222; vol. 132.

Sandoval; Ignacio V.; et al.; Lysosomal Integral Membrane Glycoproteins Are Expressed at High Levels in the Inclusion Bodies of I–Cell Fibroblasts; Archives of Biochemistry and Biophysics; 1989; pp. 157–167; vol. 271, No. 1.

Waheed, Abdul, et al; Enhanced Breakdown of Arysulfatase A in Multiple Sulfatase Deficiency; European Journal of Biochemistry; 1982; pp. 317–321; vol. 123.

copy of International Search Report; Patent Cooperation Treaty Application No. PCT/AU 97/00304, dated Aug. 15, 1997.

copy of Supplementary Partial European Search Report; application No. EP 97 92 0460, dated Jan. 21, 2002.

Hua, Chi T., et al.; Evaluation of the lysosome–associated membrane protein LAMP–2 as a marker for lysosomal storage disorder; Clinical Chemistry; 1998; pp. 2094–2102; 44:10.

Meikle, Peter J., et al.; Diagnosis of lysosomal storage disorders: evaluation of lysosome–associated membrane protein LAMP–1 as a diagnostic marker; Clinical Chemistry; 1997; pp. 1325–1335.

* cited by examiner

EARLY DETECTION OF LYSOSOMAL STORAGE DISORDERS

CROSS REFERENCES TO RELATED APPLICATION

This application is the U.S. national phase of PCT/AU97/00304, filed May 16, 1997, which claims priority from Australian patent application PN 9917, filed May 17, 1996.

The present invention relates generally to lysosomal storage disorders and to diagnostic agents for their detection in humans and other animals. More particularly, the present invention is directed to the uses of the LSD markers Lamp-1, Lamp-2. Limp-II, 4-sulphatase, acid phosphatase (ACP), β-hexosaminidase or α-mannosidase, amongst others as diagnostic agents for the detection of many lysosomal storage disorders.

Bibliographic details of the publications referred to in this specification by author are collected at the end of the description.

Throughout this specification, unless the context requires otherwise, the word "comprise", or variations such as "comprises" or "comprising" will be understood to imply the inclusion of a stated element or integer or group of elements or integers, but not the exclusion of any other element or integer or group of elements or integers.

Lysosomal storage disorders (LSD) represent a group of 39 distinct genetic diseases, each one resulting from a deficiency of a particular lysosomal protein or, in a few cases, from non-lysosomal proteins which are involved in lysosomal biogenesis. The importance of these disorders to health care becomes obvious when the group incidence rate for LSD (1:5,000 births) is compared with well known and intensively studied genetic disorders, for which newborn screening is currently performed, such as phenylketonuria (1:14,000) and cystic fibrosis (1:2,500). LSD generally affect young children and have a devastating impact on the child and the family involved. Affected individuals can present with a wide range of clinical symptoms depending upon the specific disorder and the particular genotype involved. Central nervous system dysfunction, from behavioural problems to severe mental retardation, is characteristic of many LSD. In the mucopolysaccharidoses, other symptoms may include skeletal abnormalities, organomegaly, corneal clouding and dysmorphic features (Neufeld and Meunzer, 1995). In severe cases, the child requires constant medical management of the disorder but dies before adolescence.

Except for those cases with a family history of the disease, pre-symptomatic detection of LSD can only be achieved by newborn screening. Currently, even after the presentation of clinical symptoms, the diagnosis of a LSD is a complex process involving a range of assays performed on urine, blood and in some disorders, skin fibroblasts. These assays are time consuming, expensive and invasive, making them unsuitable for newborn screening applications. In order to justify the screening of the entire neonatal population for a given disorder or group of disorders there are a number of criteria which need to be satisfied, these criteria can be summarised as two broad considerations. Firstly, does neonatal diagnosis provide clear cut benefits to the neonate and family? Secondly, are these benefits reasonably balanced by the total cost of screening?

In recent years, treatment of some LSD has become possible. Cystinosis is treated with cysteamine (Gahl et al., 1987; Markello et al., 1993), a number of LSD including mucopolysaccharidosis (MPS) I and MPS VI have been responsive to bone marrow transplants (Hoogerbrugge et al, 1995; Hopwood et al, 1993) and Gaucher disease is currently being treated by enzyme replacement therapy which, like bone marrow transplantation, is theoretically applicable to a wide range of LSD. Recombinant enzymes deficient in many of LSD have been characterised and there are now numerous animal models which are being used to evaluate enzyme replacement and gene therapies for these disorders. Animal models currently in use include dog models for fucosidosis (Taylor et al., 1989) and MPS VII (Haskins et al. 1992), cat models for MPS I, and VI (Crawley et al., 1996; Haskins et al, 1992), goat models of β-mannosidosis (Jones and Kennedy, 1993) and MPS IIID (Thompson et al., 1992) and mouse models for MPS VII (Sands et al., 1994), galactosialidosis (Zhou et al., 1995) and Niemann-Pick disease (Otterbach and Stoffel, 1995). It is probable that within the next 5 to 10 years effective therapies will be available for many of the LSD.

The effectiveness of these therapies, particularly for those LSD involving central nervous system and bone pathologies, will rely heavily upon the early diagnosis and treatment of the disorder, before the onset of irreversible pathology. Animal studies involving bone marrow transplantation in a fucosidosis dog model, which relates predominantly to central nervous system pathology (Taylor et al., 1989) and enzyme replacement therapy studies in an MPS VI cat model (predominantly bone pathology) (Crawley et al., 1996; Crawley et al., 1997) have shown a clear correlation between the age when treatment was commenced and efficacy and that enzyme replacement therapy is effective for the prevention of bone pathology.

A further consideration, critical to bone marrow transplant therapy, is that early diagnosis of the LSD will allow clinicians to take advantage of the window of opportunity presented by the naturally suppressed immune system of the neonate to maximise the chances of a successful engraftment.

Early detection of these disorders has the added advantage of permitting genetic counselling of the parents, with the option of prenatal diagnosis in subsequent pregnancies, and management of the affected child. Accurate techniques for monitoring progress of the treatment regimes are also required.

One common feature of these LSDs is the accumulation and storage of material normally degraded within the lysosome and transported across the lysosomal membrane. It is generally recognised that this results in an increase in the number and size of lysosomes within the cell from approximately 1% to as much as 50% of total cellular volume. However, although the formation of lysosomal storage vacuoles within affected cells is well-known, the process by which lysosomal biogenesis occurs, in particular the nature and role of genes and enzymes which are involved in the process, is poorly understood.

In work leading up the present invention, the inventors sought to identify proteins nucleic acid molecules, oligosaccharides, gangliosides and processes involved in lysosome biogenesis, which are capable of functioning as markers of lysosome storage disorders (hereinafter referred to as "LSD markers"). The LSD markers identified by the inventors have provided for the development of a wide range of diagnostic and therapeutic reagents for the treatment of LSDs in humans and other animals, including the development of procedures to facilitate the presymptomatic detection of all LSDs in a single assay.

Accordingly, one aspect of the present invention provides a diagnostic method of detecting a lysosomal storage disorder (LSD), monitoring the progress of an LSD or the efficacy of treatment of an LSD in a human or other animal patient comprising assaying the level of expression of an LSD marker as defined herein in a biological sample derived from said patient.

As used herein, the term "LSD marker" or similar term shall be taken to refer to an enzyme, protein, polypeptide or other biomolecule or a homologue, analogue or variant thereof derived from the lysosome of a human or other animal, the presence or level of expression of which is associated with the occurrence, development or onset of at least one LSD in said animal. An LSD marker is usually expressed in a cell derived from a patient having an LSD at a level which is different from that observed for a normal individual.

The present invention extends to the assay of an LSD marker for the diagnosis of a wide range of LSDs selected from, but not limited to the list comprising Pompe disease, Salla disease, Gaucher disease, mucopolysaccharidoses (MPS) including MPS I, MPS II, MPS IIIA, MPS IIIB, MPS IIIC, MPS IVA, and MPS VI, I-cell disease including ML II/III, Tay-Sach's disease. Fabry's disease, metachromatic leukodystrophy (MLD), Niemann-Pick disease and multiple sulphatase deficiency, amongst others.

Those skilled in the art will be aware that a marker may also be used to diagnose a genetic predisposition toward the disease which the marker is used to detect. The present invention therefore extends to the assay of an LSD marker for determining the genetic predisposition of a patient to one or more or the LSD discussed supra.

An LSD marker according to the present invention may be any lysosomal enzyme, protein, polypeptide or other biomolecule which is up-regulated as a result of the lysosomal proliferation which is characteristic of an LSD or at least accumulates at an increased rate in the lysosomes of patients suffering from an LSD. Those skilled in the relevant art will be aware that the most suitable LSD markers for the present purpose are those enzymes, proteins, polypeptides or other biomolecules which are expressed at least 2-fold, preferably at least 5-fold, more preferably at least 10-fold and even more preferably at least 20-fold higher in the cells of LSD-affected patients than in non-affected patients.

The present invention extends to the use of any one or more of Lamp-1, Lamp-2, Limp-II, mannose-6-phosphate receptors, 4-sulphatase, acid phosphatase (ACP), β-hexosaminidase, or α-mannosidase, amongst others as an LSD marker.

The invention further extends to the use of the foregoing LSD markers in the manufacture of a composition or medicament for the diagnosis and/or treatment of an LSD in a human or animal subject.

In a particularly preferred embodiment of the present invention, said LSD marker is the lysosomal Lamp-1 protein. As described in the Examples herein, the inventors have found that the level of Lamp-1, protein is elevated in a wide range of patients suffering from LSDs, when compared to the level of Lamp-1 expression in normal individuals. For example, the level of Lamp-1 protein is 3- to 6-fold higher in the plasma obtained from a patient suffering MPS I compared to a non-affected individual.

In one embodiment of the invention, the level of expression of said LSD marker is assayed by measuring the level of enzyme activity of said LSD marker. Several methods are available for the assay of particular enzymes derived from biological samples. Those skilled in the art will be aware that an assay method will vary depending upon the nature of the LSD marker in question, including its substrate preference and co-factor requirement and the tissue or organ from which it was derived. Assay methods for the lysosomal enzymes ACP, β-hexosaminidase, α-L-iduronidase and α-mannosidase are incorporated herein by way of exemplification only.

In an alternative embodiment, wherein said LSD marker is either a protein or polypeptide or other stored substrate, the level of expression of said LSD marker may be assayed by an immunoassay. Those skilled in the art are aware that, in its broadest context, an "immunoassay" comprises incubating a test sample with one or more immunointeractive molecules specific for said LSD marker, for example an antibody, for a time and under conditions sufficient for binding thereto and detecting said binding. Altered levels of the LSD marker, in particular elevated levels of the LSD marker Lamp-1, compared to the levels detected in non-affected patients, may indicate an LSD.

Conditions for incubating an antibody with a test sample vary, depending upon the format employed in the assay, the detection methods employed and the type and nature of the antibody molecule used in the assay. Those skilled in the art will recognise that any one of the commonly available immunological assay formats, for example radioimmunoassays, enzyme-linked immunosorbent assays (ELISA), diffusion-based Ouchterlony, rocket gel immunoelectrophoresis or in situ immunoassays can be readily adapted to the present purpose. Examples of such assay formats can be found in Chard (1986), Bullock (1982, 1983, 1984) or Tijssen (1985). Generally, the assay format will be selected to provide the highest sensitivity of detection for the test sample.

Immunoassays are useful in the quantification of an LSD marker in a test sample, particularly test samples derived from blood samples or isolated cells, in particular to determine whether the level of said LSD marker is elevated compared to normal levels detectable in non-affected individuals. As a consequence, such an immunoassay is of particular use in determining whether a patient may have a lysosomal storage disorder. The invention described herein extends to all such uses of immunointeractive molecules and diagnostic assays which require said immunoassays for their performance.

A wide range of immunoassay techniques may be used, such as those described in U.S. Pat. Nos. 4,016,043, 4,424, 279 and 4,018,653. By way of example only, an antibody raised against the Lamp-1 protein is immobilised onto a solid substrate to form a first complex and a biological test sample from a patient is brought into contact with the bound molecule. After a suitable period of incubation, for a period of time sufficient to allow formation of an antibody-Lamp-1 secondary complex, a second Lamp-1 antibody labelled with a reporter molecule capable of producing a detectable signal is then added and incubated, allowing sufficient time for the formation of a tertiary complex of antibody-Lamp-1-labelled antibody. Any unreacted material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein, $Eu^{3+}$ or other lanthanide metals, and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

The immunologically-interactive molecule, in particular an antibody molecule, is also useful in purifying an LSD marker protein or in the manufacture of a compound or medicament for the diagnosis and/or treatment of an LSD in a human or animal subject. Methods for the affinity purification of proteins using antibodies are well-known to those skilled in the art.

In a particularly preferred embodiment, the immunoassay employed according to the invention is an ELISA. Antibodies labelled with $Eu^{3+}$ or other lanthanide metals may also be useful as detection molecules in immunoassays based on the time delayed fluorescence, observed with these compounds.

The immunoassay test samples of the present invention may be derived from any organ, tissue or other biological sample comprising lysosomes. Accordingly, the diagnostic assay of the present invention may be carried out using test samples derived from a human or other animal of any developmental stage including a foetus, embryo, neonate or adult animal, provided that the sample contains a sufficient level of said LSD marker to be detected using a known assay format. Suitable test samples include, but are not limited to crude or partially-purified extracts from cells such as fibroblasts, cultured cell lines, urine, blood and blood-derived products such as serum or plasma, amongst others.

The test sample used in the above-described method will vary based upon the assay format, nature of the detection method and the tissues, cells or extracts used as the sample to be assayed. Methods for preparing protein extracts of cells are well-known in the art and can be readily adapted in order to obtain a sample which is suitable for the assay format selected.

In a particularly preferred embodiment of the present invention, the test sample is a blood sample or plasma, for example a blood-spot taken from a Guthrie card.

The diagnostic methods described supra are useful in antenatal screening for LSD. The invention is also of particular utility in the screening of neonates up to 7 days of age using dried blot spots collected from infants. However, the present invention extends to the use of any assay format or test sample to detect an LSD marker.

A second aspect of the present invention provides a biomolecule to facilitate the detection of a lysosomal storage disorder in a human or other animal, wherein said biomolecule is capable of binding to an LSD marker as defined herein when used in an assay to determine the level of expression of said LSD marker in a biological test sample derived from said human or other animal.

According to this aspect of the invention, said biomolecule may be an enzyme substrate molecule, a co-factor, an immunologically interactive molecule such as an antibody molecule.

In one embodiment, the biomolecule according to this aspect of the invention is an immunologically interactive molecule.

The term "immunologically interactive molecule" as used herein shall be taken to refer to a polyclonal or monoclonal antibody or a functional derivative thereof, for example a Fab, SCAB (single-chain antibody) or an antibody conjugated to an enzyme, radioactive, paramagnetic or fluorescent tag, the only requirement being that said immunologically interactive molecule is capable of binding to an LSD marker or a derivative, part, fragment, analogue or homologue thereof.

Preferably, the immunologically interactive molecule is in the form of an antibody such as a polyclonal or monoclonal antibody. The present invention extends to immunologically interactive fragments, parts, derivatives, homologues or analogues of these antibodies. Such antibodies may be in an isolated or purified form comprising at least 25% (w/w), more preferably at least 50% (w/w), even more preferably at least 60–75% (w/w) and even still more preferably at least 80–95% (w/w) of immunoglobulin on a protein basis. Alternatively, the antibodies may be present in the form of isolated hybridoma, culture supernatant, tissue extract, serum or whole blood or ascites fluid.

Conventional methods can be used to prepare the immunologically interactive molecules. By using a polypeptide comprising all or a fragment of an LSD marker as defined herein, polyclonal antisera or monoclonal antibodies can be made using standard methods. For example, any mammal, (e.g., a mouse, hamster, or rabbit) can be immunized with an immunogenic form of an antigen comprising an LSD marker to elicit an antibody response in the mammal. Techniques for conferring immunogenicity on an antigen include conjugation to carriers or other techniques well known in the art. For example, the antigen can be administered in the presence of adjuvant. The progress of immunization can be monitored by detection of antibody titers in plasma or serum. Standard ELISA or other immunoassay can be used with the immunogen as antigen to assess the levels of antibodies. Following immunization, antisera can be obtained and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (1975) as well as other techniques such as the human B-cell hybridoma technique (Kozbor et al., 1983), the EBV-hybridoma technique to produce human monoclonal antibodies (Cole et al., 1985), and screening of combinatorial antibody libraries (Huse et al., 1989). Hybridoma cells can be screened immunochemically for production of antibodies which are specifically reactive with the antigen and monoclonal antibodies isolated.

As with all immunogenic compositions for eliciting antibodies, the immunogenically effective amounts of the polypeptides of the invention must be determined empirically. Factors to be considered include the immunogenicity of the native antigen, whether or not the antigen will be complexed with or covalently attached to an adjuvant or carrier protein or other carrier and route of administration for the composition, i.e. intravenous, intramuscular, subcutaneous, etc. and the number of immunizing doses to be administered. Such factors are known in the art and it is well within the skill of immunologists to make such determinations without undue experimentation.

The term "antibody" as used herein, is intended to include fragments thereof which are also specifically reactive with a polypeptide which comprises, mimics, or cross-reacts with a B cell or T cell epitope of an LSD marker according to the embodiments described herein, in particular the Lamp-1 and 4-sulphatase. Antibodies can be fragmented using conventional techniques and the fragments screened for utility in the same manner as described above for whole antibodies. For example, F(ab')2 fragments can be generated by treating antibody with pepsin. The resulting F(ab')2 fragment can be treated to reduce disulfide bridges to produce Fab' fragments.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of a polypeptide which comprises, mimics, or cross-reacts with a B cell or T cell epitope of an LSD marker as hereinbefore defined.

The polyclonal, monoclonal or chimeric monoclonal antibodies can be used to detect and/or quantify an LSD marker or a derivative, homologue or analogue thereof in various biological materials, for example they can be used in an ELISA, radioimmunoassay or histochemical tests. Thus, the antibodies can be used to test for binding to an LSD marker or a derivative, homologue or analogue thereof in a sample or to determine B cell or T cell epitopes of an LSD marker.

Accordingly, in another embodiment of the present invention, the above-described antibodies are detectably labeled to facilitate their use in immunoassays conducted either in vitro, in vivo or in situ. Antibodies can be detectably labeled through the use of radioisotopes, affinity labels such as biotin, avidin and the like, enzyme labels such as horse radish peroxidase, alkaline phosphatase and the like, fluorescent labels such as FITC, rhodamine and the like or $Eu^{3+}$, using paramagnetic atoms, amongst others. Procedures for accomplishing such labeling are well-known in the art.

Preferably, the antibody is raised against a protein or polypeptide. However, in a particularly preferred embodiment, the present invention provides antibodies which are capable of recognising either the Lamp-1, Lamp-2, Limp-II or 4-sulphatase protein as described herein.

A further aspect of the invention contemplates a diagnostic kit for determining the level of expression of an LSD marker in a biological sample derived from a human or other animal suspected of having a lysosome storage disorder.

In a preferred embodiment of this aspect of the invention, said kit comprises in a first compartment several first containers adapted to contain an LSD marker enzyme, protein, polypeptide or a derivative, homologue or analogue thereof in recombinant or synthetic form and optionally adsorbed thereto, and several second containers adapted to contain an antibody which recognises said LSD marker or a B cell or T cell epitope thereof, wherein said antibody is optionally labelled with a reporter molecule capable of producing a detectable signal as hereinbefore described. There are also provided several third containers which contain a second antibody which recognises the first antibody and is optionally conjugated to a reporter molecule. If the reporter molecule is an enzyme, then several fourth containers are provided which contain a substrate molecule for said enzyme to facilitate detection of the enzyme:antibody:LSD marker complex or alternatively, the enzyme:antibody:antibody:LSD marker complex where a second antibody has been used. The reporter molecule used in this kit may also be a radio-isotope, a fluorescent molecule, or bioluminescent molecule, amongst others.

Optionally, the kit may further be contained in a package which comprises microtitre wells in one section, in which reactions may be performed. Accordingly, in one embodiment, the microtitre wells may be the equivalent of the first compartment hereinbefore described and contain the LSD marker or a derivative, homologue or analogue thereof, adsorbed thereto.

Optionally, the first, second, third and fourth containers of said kit may further be colour-coded for ease-of use.

In an exemplified use of the subject kit, the contents of the first container may be bound to a microtitre well contained in the package, if not provided in a format where said contents are already adsorbed to said microtitre well, and a biological sample to be tested is added and incubated for a time and under conditions sufficient for an antigen-antibody complex to form in said microtitre well. Following a washing step to remove unbound antibodies and other unbound protein, the contents of the third container are added to the antigen-antibody complex contained in the microtitre well and the reaction allowed to proceed for a time, and under conditions sufficient to allow the formation of the tertiary antigen-antibody-antibody complex. A control reaction may be performed in which the contents of the second container are added to the contents of the first container for a time and under conditions suitable for the formation of an antigen-antibody complex. If the antibody of the second container is not labelled with a reporter molecule, then the contents of the third container may be added for a time and under conditions suitable for the formation of a tertiary antigen-antibody-antibody complex to form. The tertiary antigen-antibody-antibody complexes of the control reaction and the test sample are then subjected to a detecting means. Alternatively, if the contents of the second container are labelled with a reporter molecule the antigen-antibody complex of the control reaction may be subjected directly to a detecting means. The means of detection of a secondary antigen-antibody or a tertiary antigen-antibody-antibody complex are numerous, as hereinbefore described and will be known to those skilled in the art. Where said means is an enzyme reaction, the contents of the fourth container are added to said secondary or tertiary complex thus formed for a time and under conditions suitable to enable the enzyme reaction to occur.

In analysing the results obtained using the subject kit, the amount of LSD marker contained in the control reaction is predetermined to provide a result which is consistent with the result obtained for a normal non-affected patient and therefore the control reaction provides a basis for comparison with the test sample. A signal obtained for the test sample which is higher than that of the control indicates a higher level of the subject LSD marker being tested. Such a result may indicate that the patient is suffering from a lysosomal storage disorder.

The present invention further extends to any kit comprising a biomolecule which is capable of detecting a lysosomal storage disorder in a human or other animal, wherein said kit is in a form which is suitable for an assay to detect expression of an LSD marker as hereinbefore defined. The present invention also extends to kits comprising multiple of said biomolecules to facilitate the detection of more than one LSD marker.

For the purposes of exemplification only, the present invention is further described by the following Figures and Examples.

In the Figures:

FIG. 1 is a graphical representation showing the cross-reactivity of polyclonal antisera raised against immunopurified LAMP-1. Microtitre wells were coated with polyclonal antibody at a level of either 5 µg/ml (○) or 10 µg/ml (□) using the one-step quantification method as described in Example 3.

Figure 2:
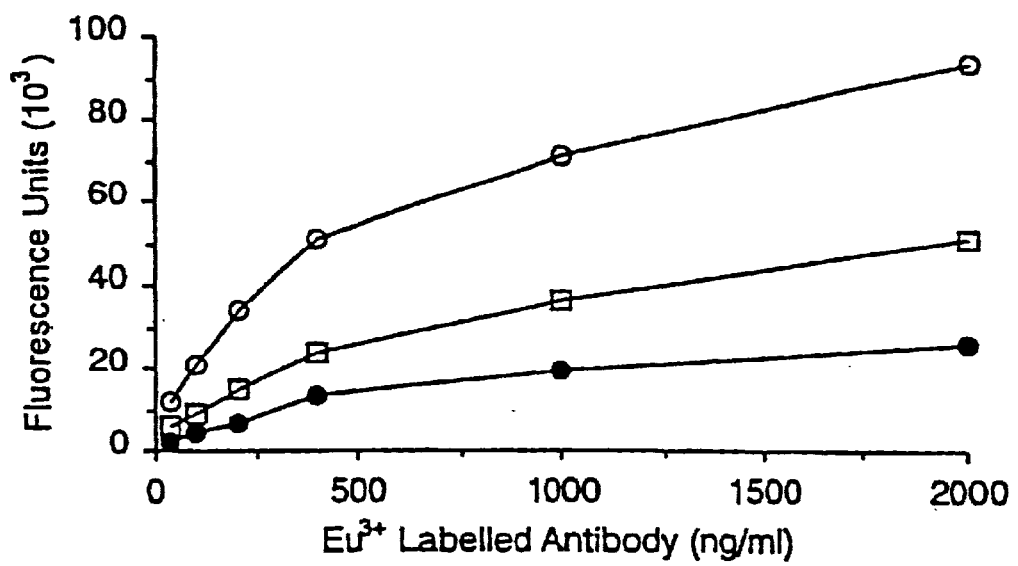

FIG. 2 is a graphical representation showing the cross-reactivity of $Eu^{3+}$-labelled antibody to LAMP-1. Standard solutions of LAMP-1 containing either 10 ng/ml (●), 20 ng/ml (□) or 40 ng/ml (○) were prepared and the fluorescent response for each sample was determined at a range of $Eu^{3+}$ labeled antibody concentrations in the time delayed fluorescence immunoassay, using the one-step quantification method as described in Example 3.

Figure 3:
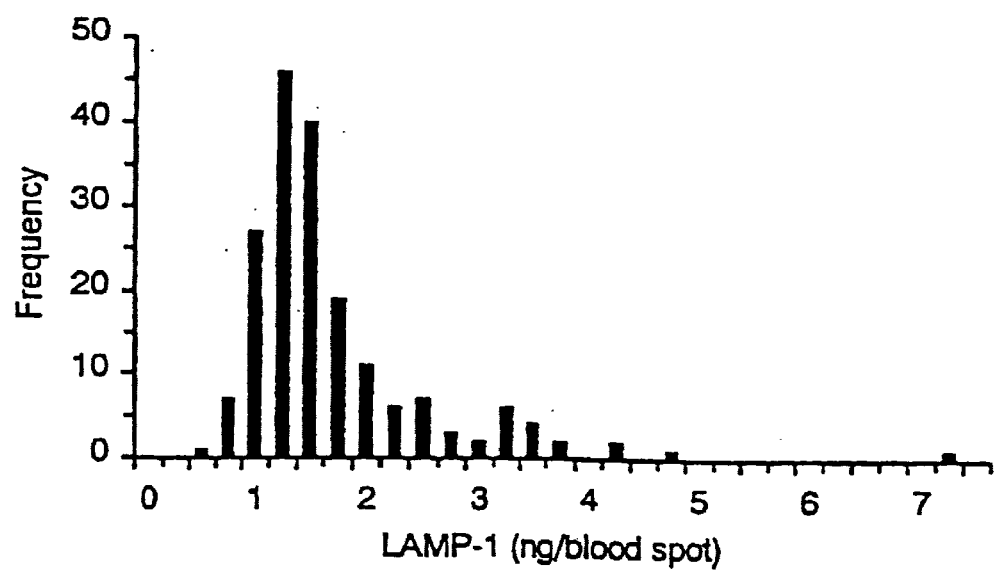

FIG. 3 is a graphical representation showing LAMP-1 levels in blood spots from 186 newborns, as determined using the one-step quantification method described in Example 3. The x-axis indicates the level of LAMP-1 (ng/blood spot). The number of individuals within each range of LAMP-1 levels is indicated on the y-axis.

Figure 4:
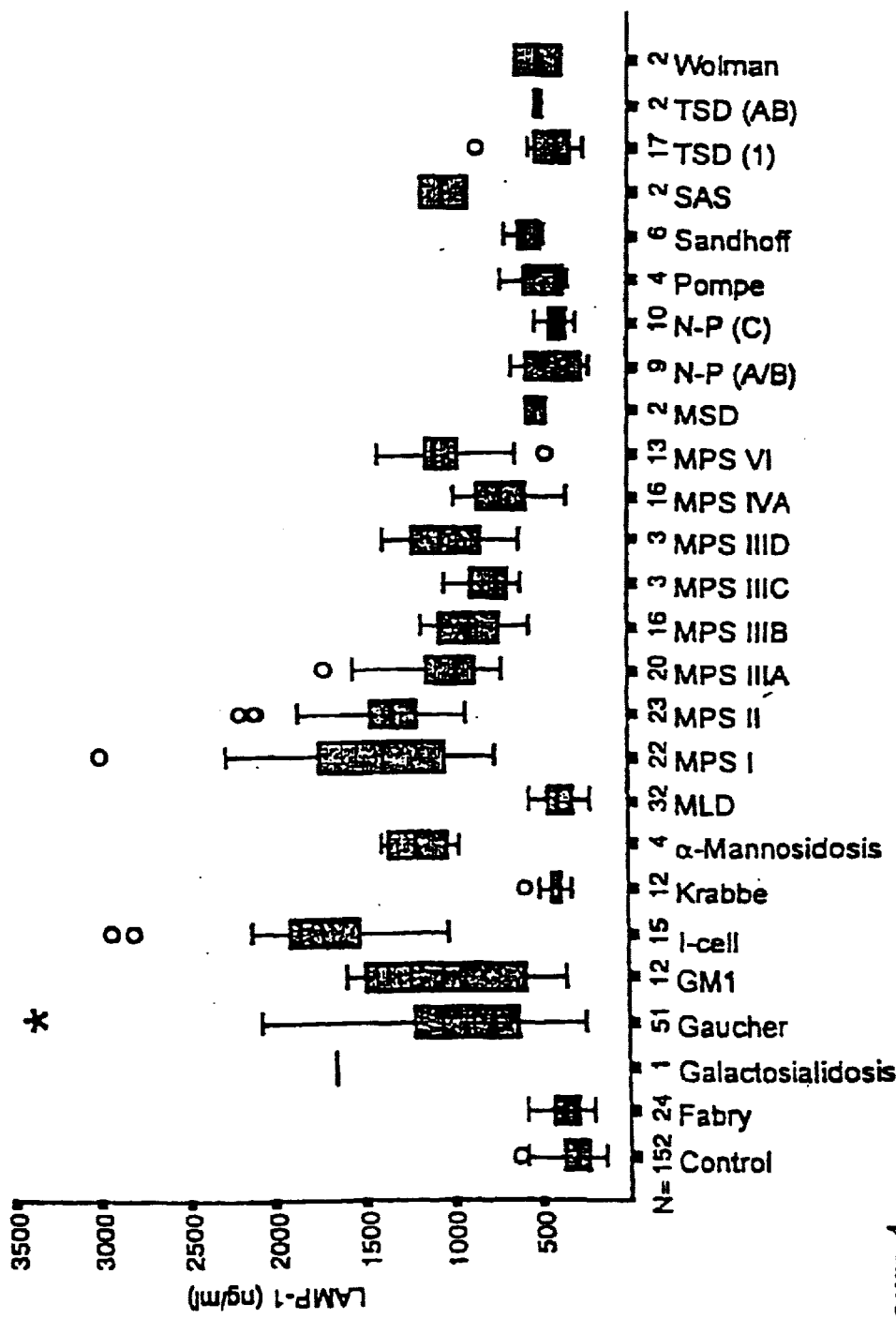

FIG. 4 is a graphical representation showing LAMP-1 levels in plasma from 320 LSD affected individuals, representing 25 lysosomal storage disorders, and 152 unaffected individuals. LAMP-1 levels were determined using 5–10 µl samples in the two-step quantification method described in Example 3. Centre bars show the median LAMP-1 level for each disorder, shaded area shows the $25^{th}$ and $75^{th}$ percentiles and the upper and lower bars show the limits of the range. Outliers (○) and extreme outliers (*) are also indicated. GM1=GM1 gangliosidosis: MLD=metachromatic leukodystrophy; MSD=multiple sulphatase deficiency; N-P=Niemann-Pick; SAS=sialic acid storage, TSD=Tay Sachs disease.

Figure 5:
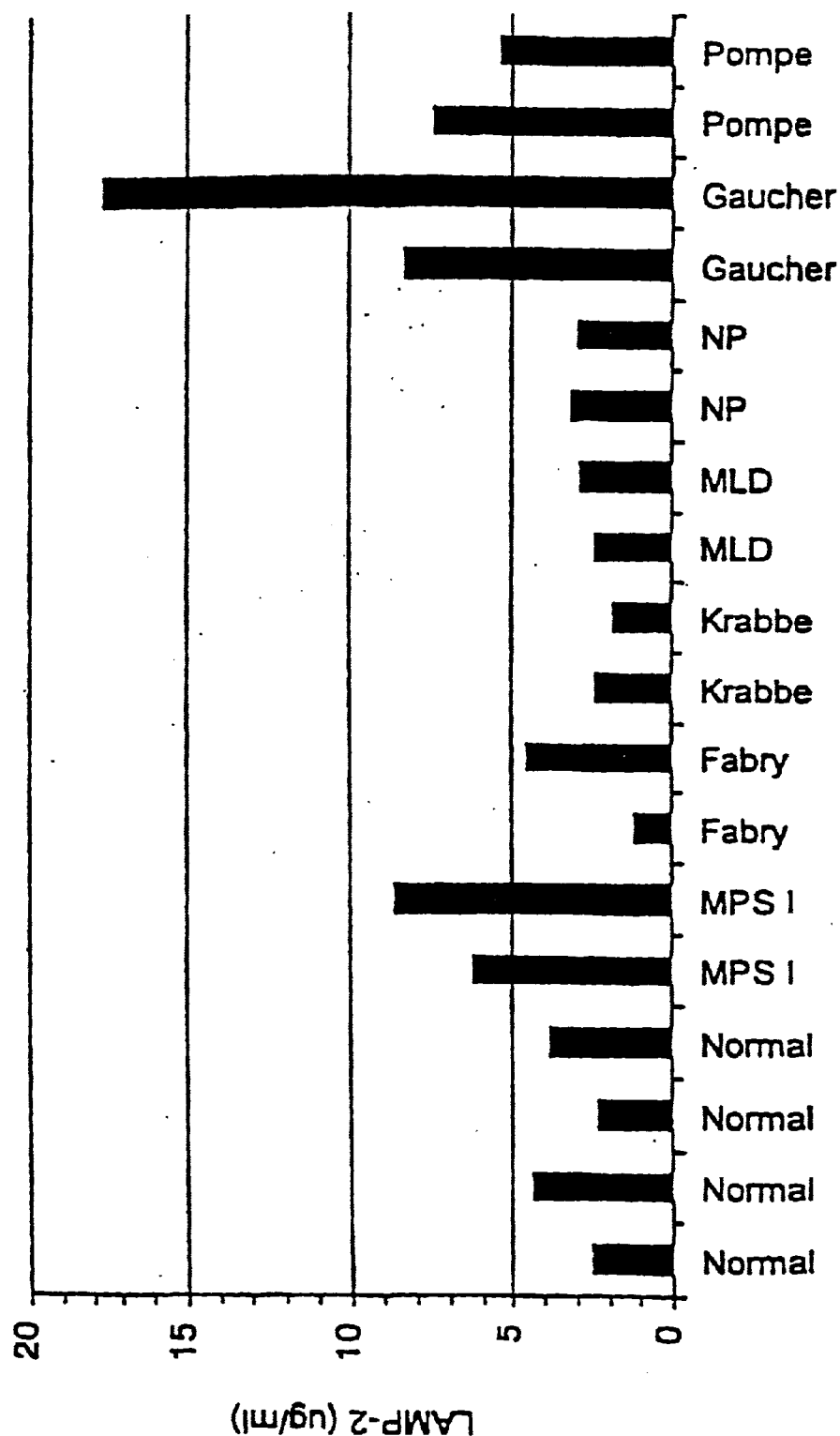

FIG. 5 is a graphical representation showing the LAMP-2 levels in plasma samples derived from 14 LSD affected and 4 (Normal) unaffected individuals. The status of individuals is indicated on the x-axis.

Figure 6:
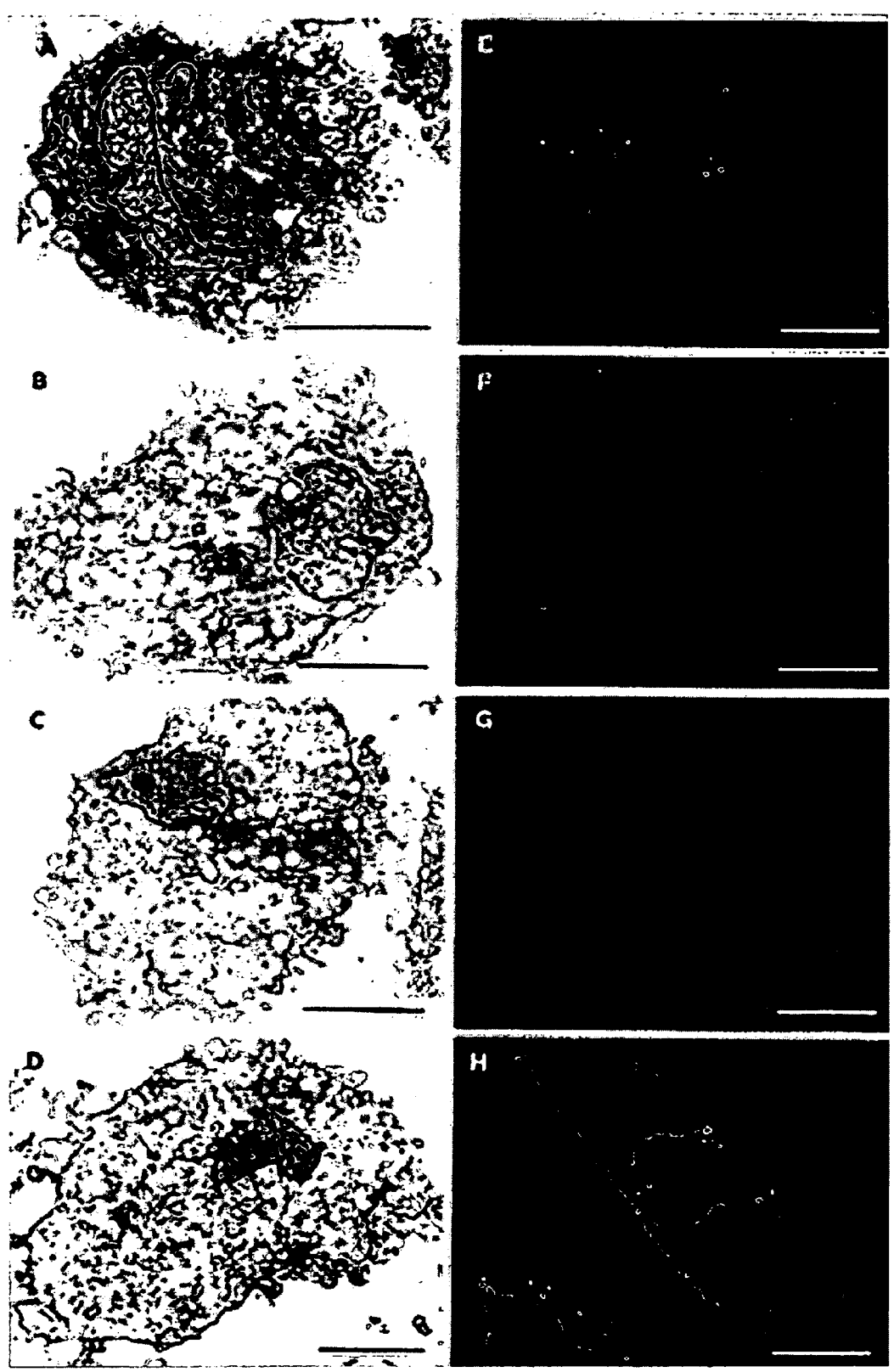

FIG. 6 is a photographic representation of electron and immunofluorescence micrographs of fibroblasts from the Sucrosome Model. Panels A, B, C, & D are electron micrographs of fibroblasts grown in media containing 100 mM sucrose for (A) 0 days; (B) 1 days; (C) 7 days; (D) 28 days. Panels E, F, G, & H are immunofluorescence micrographs of fibroblasts grown in media containing 100 mM sucrose for (E) 0 days; (F) 1 day; (G) 7 days; (H) 28 days. Immunofluorescence micrographs were photographically exposed for equivalent times (45 sec) to enable comparison of relative intensities. Scale bar is 4µ for EM micrographs and 20µ for immunofluorescence micrographs.

Figure 7:
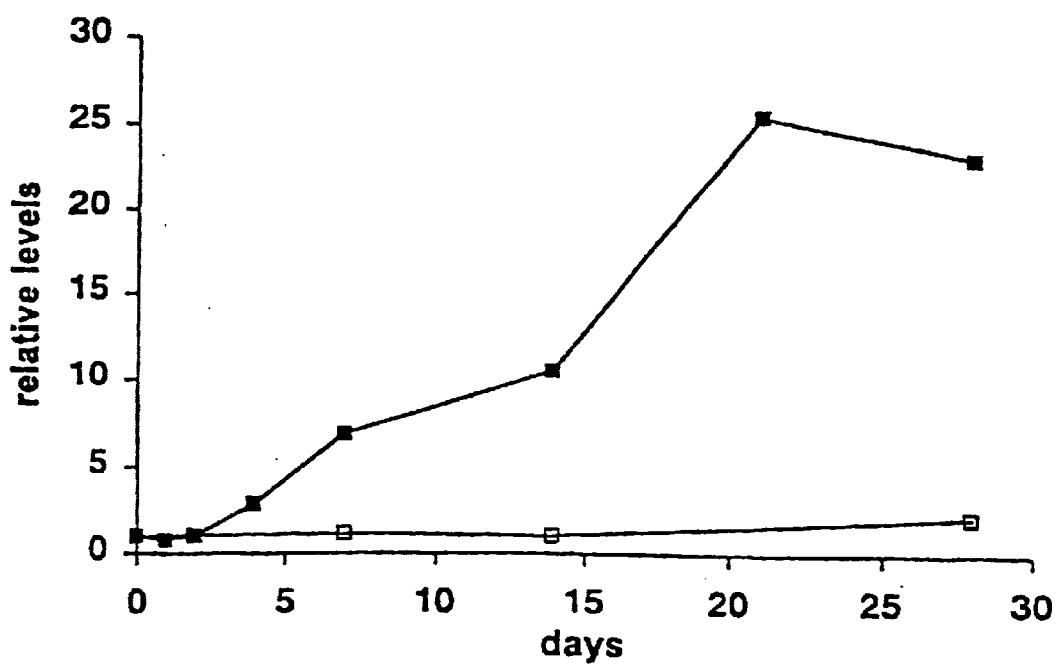

FIG. 7 is a graphical representation showing the relative LAMP-1 protein levels in the Sucrosome Model. Skin fibroblasts were grown in the presence or absence of 100 mM sucrose for up to 28 days. Cells were harvested at set time points and the LAMP-1 determined in cells grown in the presence (■) and absence (□) of sucrose. LAMP-1 values were normalized to total protein content.

Figure 8:
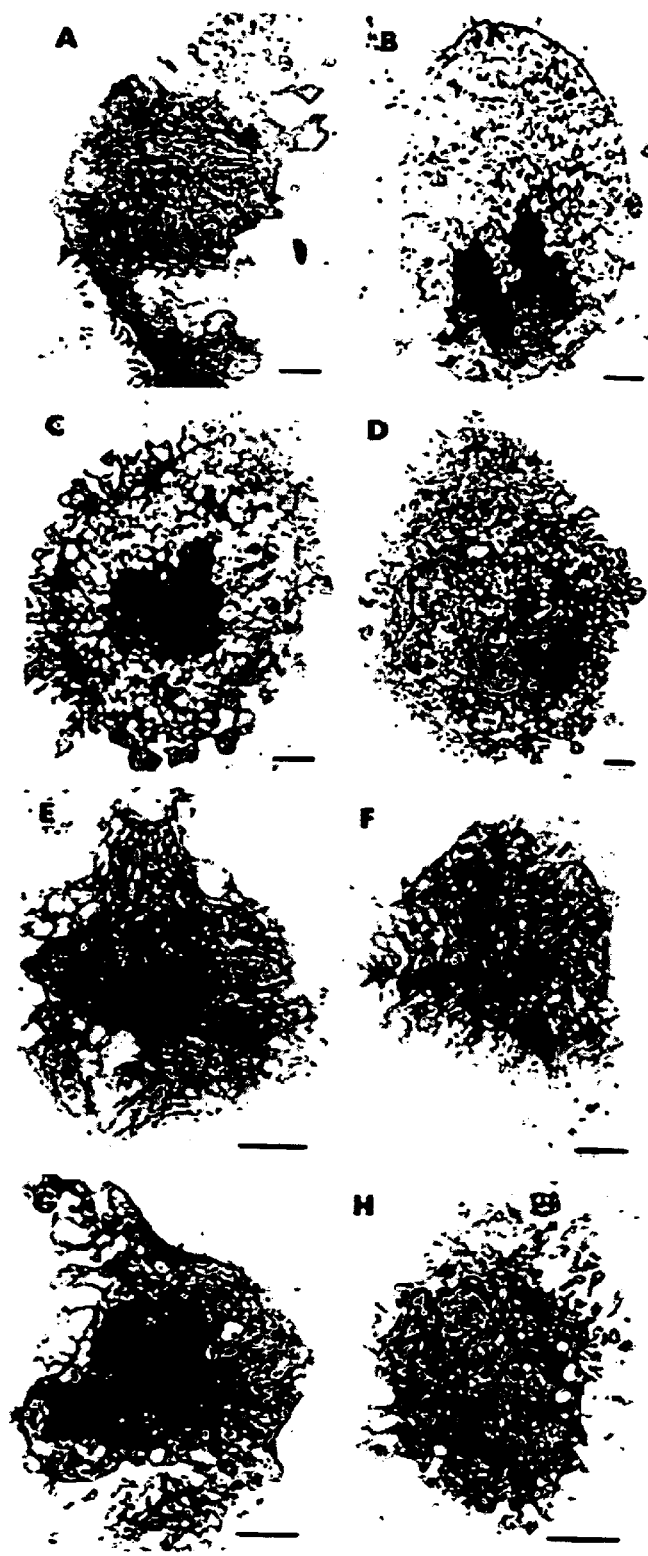

FIG. 8 is a photographical representation of electron micrographs showing the correction of storage in the Sucrosome Model. Electron micrographs of fibroblasts grown on normal media (Panel A) or sucrose containing media (Panels B–H). Cells were grown for 14 days and either harvested immediately (Panels A and B), switched onto BME media and harvested after 1 day (Panel C); 3 days (Panel E) and 7 days (Panel G) or switched onto media containing invertase and harvested after 1 day (Panel D); 3 days (Panel F) and 7 days (Panel H). Scale bar is 2µ.

Figure 9:
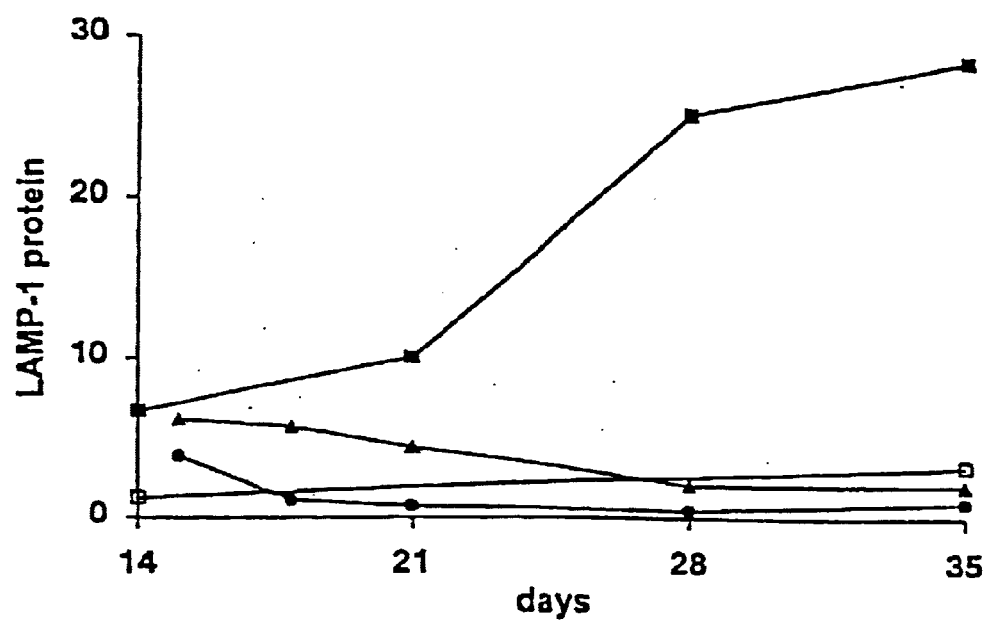

FIG. 9 is a graphical representation showing the relative levels of LAMP-1 protein after correction of storage on the Sucrosome Model. Skin fibroblasts were grown in the presence of sucrose for 14 days to accumulate storage vacuoles. The cells either continued to grow in media containing sucrose or were corrected by switching the cells to BME media or to BME media containing invertase for up to a further 21 days. LAMP-1 was determined at time points through the 21 day period and plotted. Cells were grown on sucrose containing media only (■), or on sucrose containing media for 14 days then placed on BME media (▲), or on sucrose containing media for 14 days then placed on invertase containing media (●), or on BME media throughout the time-course (□).

Figure 10:
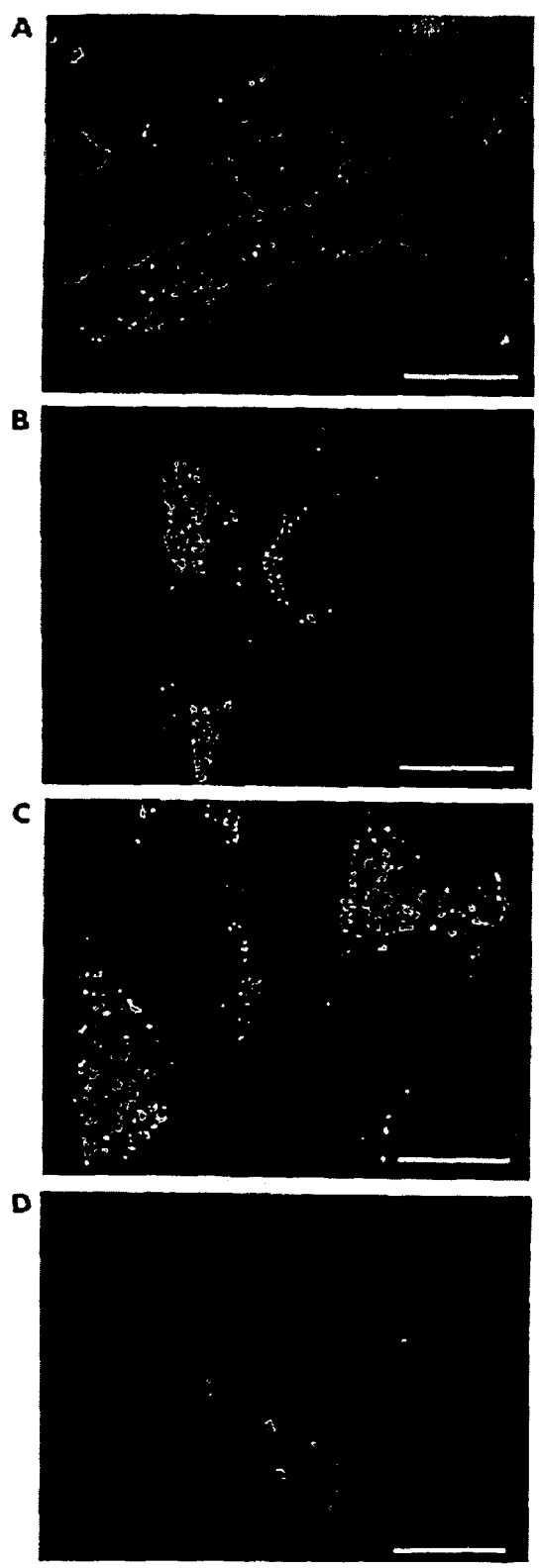

FIG. 10 is a photographic representation of immunofluorescence micrographs showing fibroblasts from affected cell-lines labelled using anti-LAMP-1 monoclonal antibody. Fibroblasts were from Pompe (Panel A), Salla (Panel B), MPS-II (Panel C), and MPS-VI (Panel D) affected cell-lines. Micrographs were photographically exposed for equivalent times (45 sec) to enable comparison of relative intensities. Scale bar is 20µ.

Figure 11:
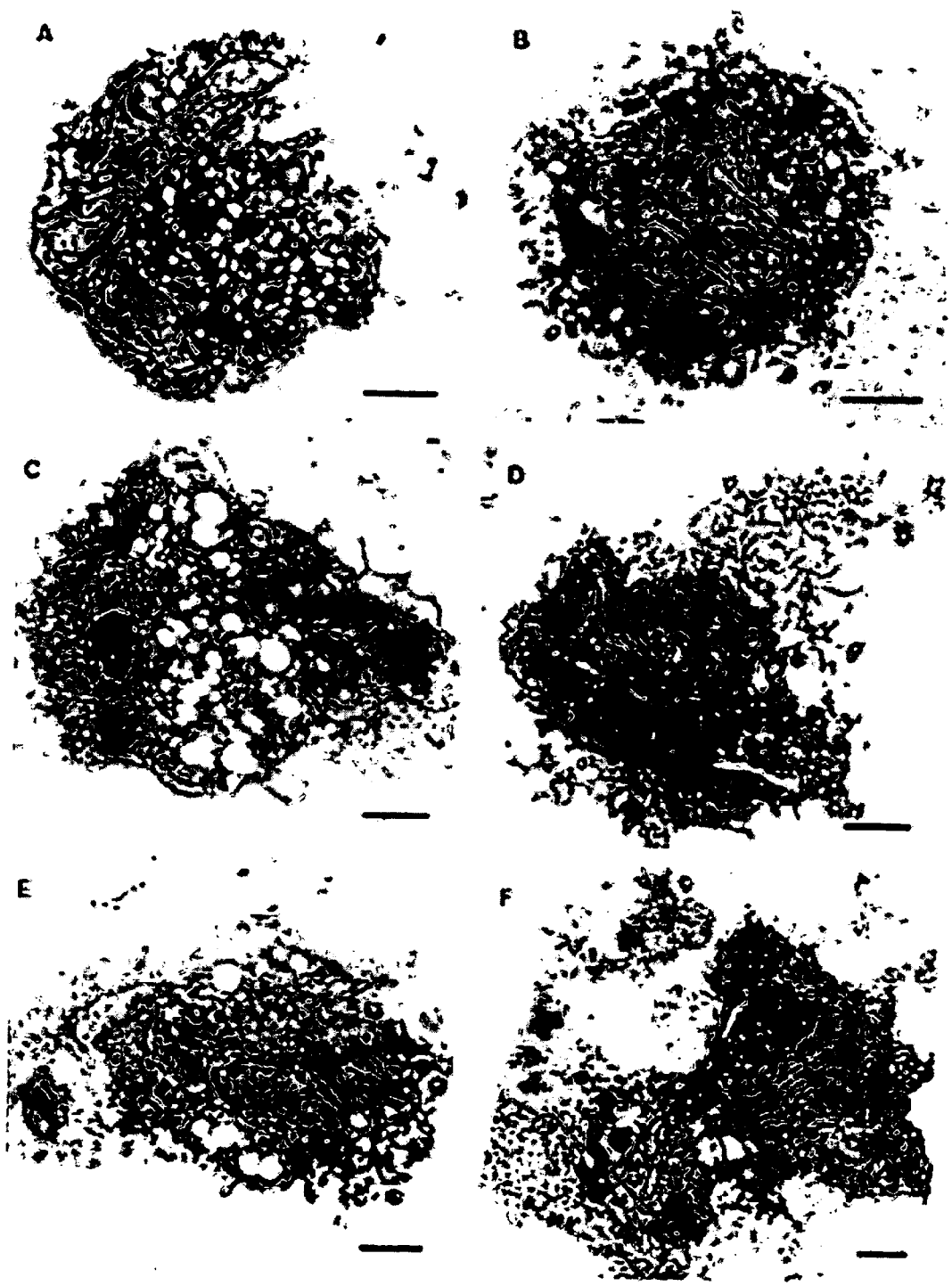

FIG. 11 is a photographic representation of electron micrographs showing correction of storage in patient cell-lines. Cell lines were from a Pompe affected cell (Panel A): Pompe corrected cell (Panel B); MPS-II affected cell (Panel C); MPS-II corrected cell (Panel D); MPS-VI affected cell (Panel E); MPS-VI corrected cell (Panel F). Electron microscopy confirmed correction in Pompe (Panels A & B), MPS-II (Panels C & D) and MPS-VI (Panels E & F) affected cells, with the size of storage vacuoles dramatically decreasing (Panels B,D,F) within 7 days after the addition of the enzyme. Scale bar is 2μ.

Figure 12:
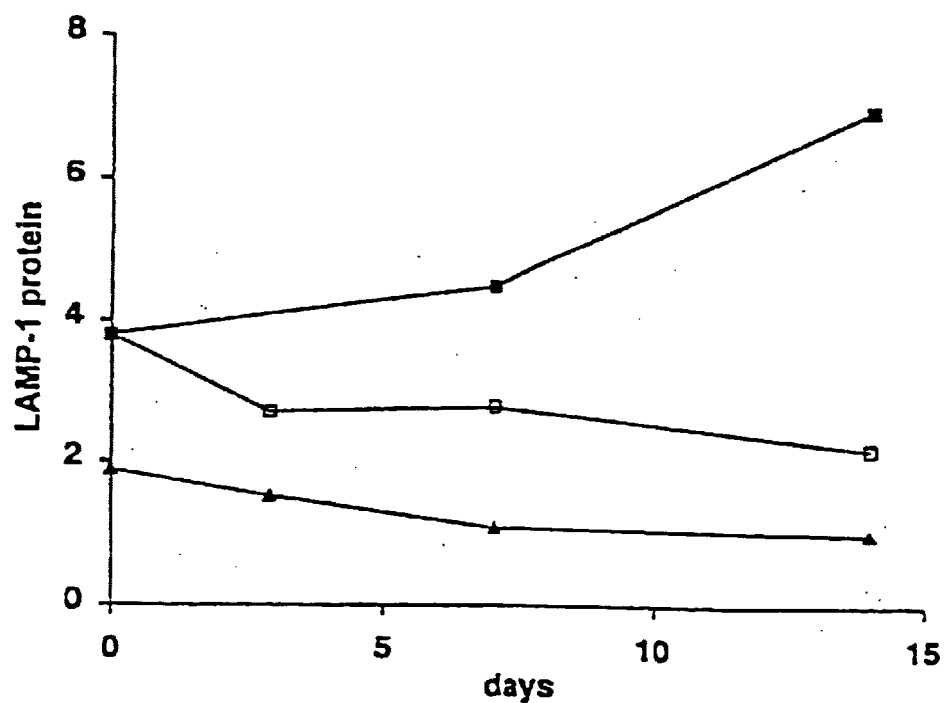

FIG. 12 is a graphical representation showing relative LAMP-1 levels in Pompe-affected fibroblasts and corrected Pompe fibroblasts. Pompe affected fibroblasts and normal skin fibroblasts were grown to confluency then either continued on normal media or corrected by switching the cells to media containing α-glucosidase for up to a further 14 days. Relative LAMP-1 levels were determined at time points through the second 14 day period and plotted. Normal cells are represented by (▲), Pompe affected cells on BME media by (■) and Pompe affected cells on α-glucosidase containing media by (□).

EXAMPLE 1

Production of Antibodies Against LAMP-1.

Anti-LAMP-1 monoclonal antibody (clone BB6) and anti-LAMP-1 polyclonal antibody have been described previously and are reasonably available to the public (Carlsson and Fukuda, 1989: Dahlgren et al. 1995). For the production of the anti-LAMP-1 monoclonal antibody clone 4F5, mice were immunised with lysosomal membranes purified from human placenta (Meikle et al., 1995). Membranes were denatured by boiling in 1% (v/v) 2-mercaptoethanol for 5 min and the pelleted membranes extracted with chloroform/methanol (2:1)×2. Female Balb/C mice were immunised according to the following schedule, 50 μg antigen in 400 μl PBS by intra-splenic injection, 14 days later 50 μg antigen in 200 μl of PBS/incomplete Freund's adjuvant emulsion by intraperitoneal injection, 21 days later 50 μg antigen in 200 μl PBS by intraperitoneal injection. Four days later the spleen cells were harvested and fused with P3.653 myeloma cells as described by Zola and Brooks (1982).

EXAMPLE 2

Purification of LAMP-1

Total membranes from human placenta were prepared as follows, fresh placenta (450 g) was dissected into 1–2 cm strips and washed three times with cold 0.25 M sucrose, 1 mM EDTA, pH 7.0 then minced and homogenised (Omnimix 1 min, full speed) in 800 ml of the same buffer. The cell debris were pelleted at 750×g for 10 min and homogenised a further two times. The supernatants were combined, filtered through cotton gauze and made up to 10 mM $CaCl_2$. After 1 h at 4° C. the placental membranes were pelleted at 10,000×g for 90 min. The membranes were resuspended in 1 M NaCl (320 ml) freeze/thawed 3 times then pelleted at 100,000×g for 1 h. The 1 M NaCl wash was repeated and the membranes finally taken up into 320 ml of solubilisation buffer (50 mM MOPS, 1 mM EDTA, 150 mM NaCl, 10%(v/v) glycerol, 1%(w/v) Thesit, pH 7.0) and stirred at 4° C. for 16 h. The insoluble material was pelleted at 100.000×g for 1 h and the supernatant recovered.

The supernatant was made up to 3 mM $CaCl_2$, 3 mM $MgCl_2$ then applied to a 70 ml column of concanavalin A Sepharose (Pharmacia Biotech, Uppsala, Sweden) pre-equilibrated in solubilisation buffer containing the $CaCl_2$ and $MgCl_2$. The column was washed with the same buffer and the bound proteins including LAMP-1 were eluted by solubilisation buffer containing 10% (w/v) α-methyl mannoside. The eluate was applied to a 5 ml column of Red Dye No. 78 (Centre for Protein and Enzyme Technology, LaTrobe University, Bundoora Australia) and the LAMP-1 recovered in the flow through.

Anti-LAMP-1 monoclonal antibody 4F5 (20 mg) was coupled to Affigel (10 ml) and used for the affinity purification of LAMP-1. The Red Dye flow through (120 ml) was mixed with the anti-LAMP-1 affinity gel and rocked gently for 16 h at 4° C. the gel was then poured into a column and washed with PBS. The LAMP-1 was eluted from the column with 100 mM triethylamine, pH 11.5, dialysed against water and lyophilised.

The preparation of total placental membranes resulted in a LAMP-1 yield of only 25% of the total LAMP-1 present in the placenta, despite the fact that greater than 60% of the lysosomal membrane enzyme acetyl coenzyme A:α-glucosaminide N-acetyltransferase was associated with these membranes.

However, solubilisation of the membranes, chromatography on concanavalin A Sepharose and subsequent red dye chromatography all gave greater than 80% recovery of LAMP-1. From a single placenta, approximately 1 mg of LAMP-1 was recovered in the red dye column flow through.

The successive immunoprecipitation of the LAMP-1 from this sample resulted in the recovery of approximately 100 μg per precipitation.

Purified LAMP-1 appeared as a homogeneous band on coomassie stained SDS-PAGE (not shown), was quantified by the bicinchoninic acid method and subsequently used as a standard for the immunoquantification of LAMP-1 protein.

EXAMPLE 3

Immunoquantification of LAMP-1

Methods

Determination of LAMP-1 was performed using a Time Resolved Fluorescence Immunoassay (TRFIA). In this assay, the detecting antibody is labelled with a lanthanide metal (usually europium) chelated into $N^1$-(p-isothiocyanatobenzyl)-diethylenetriamine-$N^1$, $N^2$, $N^3$, $N^3$-tetraacetic acid. Detection of the labelled antibody is achieved by lowering the pH to release the $Eu^{3+}$ from the antibody and the subsequent complex formation with 2-napthoyltriflouroacetone and tri-n-octylphosphine oxide. The complex formed is highly fluorescent with a relatively long half-life which enables the use of time resolved fluorescence detection to eliminate background interferences (Diamandis, 1988; Hemmila, 1988).

Anti-LAMP-1 monoclonal antibody (clone BB6) was labeled with europium using the DELFIA® $Eu^{3+}$-labeling kit (Wallac Inc. North Ryde, Australia). The labeled antibody was purified from aggregated antibody and free $Eu^{3+}$ label on a Pharmacia Superose 12 Fast Phase Liquid Chromatography column (1.5×30 cm) eluting with 50 mM TRIS/HCl, pH 7.8, 0.9% (w/v) NaCl. The level of $Eu^{3+}$ conjugated to each antibody molecule was determined from protein and fluorescence levels of the conjugate.

Samples were assayed for LAMP-1 by either a one-step or two-step method.

In the one-step method, microtitre plates (Immulon 4 Dynatech Laboratories, Inc. Virginia, USA) were coated with anti-LAMP-1 polyclonal antibody at 5 μg/ml for 4 h at 37° C. (100 μl/well diluted in 0.1 M $NaHCO_3$) and washed with DELFIA® wash buffer (×6). Samples were diluted in DELFIA® assay buffer containing 200 ng/ml of $Eu^{3+}$ labeled anti-LAMP-1 monoclonal antibody (100 µl/well) and incubated in wells overnight at 4° C. Plates were incubated at room temperature for 1 h then washed (×6). DELFIA® enhancement buffer (200 µl per well) was added, the plates shaken for 10 min at room temperature and the fluorescence measured on a 1234 DELFIA® Research Fluorometer.

In the two-step method, if samples contained chemicals which were incompatible with the $Eu^{3-}$ label (e.g. EDTA, citrate), the plates were coated with the polyclonal antibody and washed as described supra; samples were diluted in DELFIA® assay buffer without the $Eu^{3+}$ labeled antibody and incubated overnight at 4° C., incubated at room temperature for 1 h and washed (×6). Assay Buffer containing 200 ng/ml of $Eu^{3+}$ labeled anti-LAMP-1 monoclonal antibody (100 µl) was added to each well and incubated at room temperature for 2 h. Plates were then washed (×6), enhancement buffer was added and the fluorescence measured as described.

For determination of LAMP-1 in blood spots, the one-step method was used with the following modifications:

Blood spots were incubated with 200 µl of assay buffer containing 200 ng/ml of $Eu^{3+}$ labeled anti-LAMP-1 monoclonal antibody. The plates were shaken for 1 h at room temperature prior to the overnight incubation at 4° C., then again for 1 h at room temperature prior to washing and addition of enhancement buffer.

Results

Labeling of the BB6 monoclonal antibody with $Eu^{3+}$ resulted in approximately 5 $Eu^{3+}$ atoms per antibody molecule. When used in the one-step immunoquantification assay as described, this gave a linear response over the range 0.1 ng –12.5 ng/well LAMP-1. A lower response was obtained with plates coated with 5 µg/ml polyclonal antibody as compared to 10 µg/ml (FIG. 1). The two-step assay gave approximately 50% of the signal of the one-step assay with a linear range up to 25 ng/well. A linear response was also observed when whole blood or plasma from either unaffected or LSD affected individuals was assayed (1–50 µl). The intra-assay coefficient of variation was less than 9%. The inter-assay variation, as determined from the coefficients of variation of the standard curve points over 9 assays performed on 4 different days, ranged from 2% to 9% across the linear range of the assay. The standard curves were subject to linear regression analysis and gave values for the standard error of estimate of between 0.14 and 0.45 ng/well with an average of 0.26 ng/well, the intercept values had an average of 0.08 ng/well with a standard deviation of 0.16 ng/well.

Precision studies were also performed on plasma samples. Five plasma samples ranging in LAMP-1 concentration from 300 to 1200 ng/ml were assayed in triplicate on 10 separate occasions, the intra-assay variation was less than 6% while the inter-assay variation was less than 8%.

Analytical recovery studies were performed by adding a known amount of purified LAMP-1 to varying amounts of plasma in the 2-step assay, the results showed an inverse relationship between the level of plasma and the recovery of exogenously added LAMP-1. When 10 ml of plasma was included per well (the largest volume assayed) recovery of exogenous LAMP-1 was 68%.

The effect of the concentration of $Eu^{3+}$ labeled antibody on the assay was also investigated. Data presented in FIG. 2 indicate that the increase in signal showed an almost linear correlation with antibody concentration up to 400 ng/ml.

In all experimental assays performed, 200 ng/ml of labeled antibody resulted in suitable sensitivity.

EXAMPLE 4

LAMP-1 Levels in Blood

Patient Samples

Blood spots used in this study were part of the routine samples collected from neonates from the South Australian population. Plasma samples used were from samples submitted to the National Referral Laboratory for LSD screening and samples processed for routine biochemistry.

Blood Spots

To determine the suitability of LAMP-1 as a marker for newborn screening for LSD, we immunoquantified the LAMP-1 present in blood spot samples taken from 186 unaffected newborns. We observed a characteristic skewed distribution with a median of 1.3 ng/spot and the $5^{th}$ and $95^{th}$ percentiles at 0.76 and 3.3 ng/spot respectively (FIG. 3). There was no correlation between LAMP-1 level and age, sex or birth weight of the newborns.

Plasma

To investigate the levels of LAMP-1 in LSD affected individuals we retrieved plasma samples from the Departmental archives of 320 LSD affected individuals, representing 25 disorders and 152 age matched (median=7, range= 0–66) unaffected individuals. LAMP-1 levels in these samples (FIG. 4) showed a tight distribution in the normal population with a median of 303 ng/ml and the $5^{th}$ and $95^{th}$ percentiles at 175 and 448 ng/ml respectively. The majority of the LSD affected individuals had LAMP-1 levels which were above the normal range (72% above the $95^{th}$ percentile of the control population), with some individuals having up to 10 times the median level of the control population.

When analysed by individual disorder, 16 of the 25 disorder groups tested were observed to have greater than 88% of individuals above the $95^{th}$ percentile of the control population, with 12 groups having 100% above the $95^{th}$ percentile (Table 1).

A significant correlation was observed between LAMP-1 levels and age in the normal population, with a Pearson correlation coefficient of –0.37 and a significance level less than 0.001. Of the affected groups, only Fabry and Gaucher had sufficient numbers and age range to test for a correlation. The Fabry group showed a Pearson correlation coefficient of –0.49 with a significance level of 0.02, whereas the Gaucher group showed no significant correlation between LAMP-1 levels and age.

Whole Blood

Samples of whole blood from six unaffected individuals were fractionated and the proportion of LAMP-1 present in white cells, red cells, and plasma was determined. Peripheral blood leucocytes and plasma were isolated from whole blood collected in heparinised tubes by the method of Kampine et al. (1967) and the white cell pellet was resuspended in saline containing 1% (v/v) Nonidet P-40 (lysis buffer). Red cells isolated in the same procedure were washed twice with saline before being resuspended in lysis buffer. The saline washes were centrifuged to pellet the white cells which were combined with the original white cell pellet, the supernatants were pooled with the plasma for determination of LAMP-1 protein.

Whole blood samples had an average of 226±31 ng/ml of LAMP-1, with the distribution of LAMP-1 being 53±7% in the plasma, 32±5% in the red blood cell pellet and 15±5% in the white cell pellet.

TABLE 1

Detection of Lysosomal Storage Disorders Based on Elevated LAMP-1 Levels in Plasma

| Disorder | Stored Substrates | N =[a] | Age[b] | Median[c] | % > 95[d] |
|---|---|---|---|---|---|
| Control | | 152 | 7 (0–66) | 308 | 5 |
| Fabry | α-galactosyl-sphingolipids: oligosaccharides | 24 | 27 (4–47) | 359 | 25 |
| Galactosialidosis | oligosaccharides | 1 | 16 | 1653 | 100 |
| Gaucher | glucoceramide | 51 | 12 (0–68) | 956 | 92 |
| GM1-gangiiosidosis | GM1-gangliosides: oligosaccharides: glycolipids: keratan sulphate | 12 | 1 (0–15) | 1071 | 92 |
| I-cell | glycolipids: oligosaccharides | 15 | 3 (0–25) | 1815 | 100 |
| Krabbe | galactoceramides | 12 | 0.4 (0–1) | 407 | 17 |
| α-Mannosidosis | α-mannosides | 4 | 4 (3–15) | 1181 | 100 |
| Metachromatic Leukodystrophy | sulphatides | 32 | 3 (0–30) | 379 | 19 |
| MPS[e] | dermatan sulphate: heparan sulphate | 22 | 1 (0–29) | 1470 | 100 |
| MPS II | dermatan sulphate: heparan sulphate | 23 | 3 (0–11) | 1406 | 100 |
| MPS IIIA | heparan sulphate | 20 | 4 (1–17) | 1039 | 100 |
| MPS IIIB | heparan sulphate | 16 | 3 (2–21) | 880 | 100 |
| MPS IIIC | heparan sulphate | 3 | 11 (6–20) | 787 | 100 |
| MPS IIID | heparan sulphate | 3 | 3 (0–3) | 1010 | 100 |
| MPS IVA | keratan sulphate | 16 | 3 (0–12) | 699 | 88 |
| MPS VI | dermatan sulphate | 12 | 4 (0–16) | 1018 | 92 |
| Multiple sulphatase deficiency | sulphatides: glycolipids; GAG[f] | 2 | 5 (3–7) | 507 | 100 |
| Niemann-Pick (A and B) | sphingomyelin | 9 | 22 (1–44) | 385 | 33 |
| Niemann-Pick (C) | cholesterol: sphingomyelin | 10 | 12 (0–41) | 391 | 20 |
| Pompe | glycogen | 4 | 0.4 (0–1) | 462 | 25 |
| Sandhoff | GM2-gangliosides: oligosaccharides | 6 | 1 (1) | 565 | 100 |
| Sialic Acid Storage | sialic acid: glucuronic acid | 2 | 2 (0–3) | 1035 | 100 |
| Tay-Sachs (1) | GM2-gangliosides: oligosaccharides | 17 | 1 (0–27) | 425 | 41 |
| Tay-Sachs (AB) | GM2-gangliosides | 2 | 7 (6–8) | 489 | 100 |
| Wolman | cholesterol esters | 2 | 1 (0–1) | 496 | 50 |

[a]Number of patient samples in each group.
[b]Median age of patients in each group, bracketed numbers indicate the range of ages of patients in each group.
[c]Median value of Plasma LAMP-1 expressed as ng/ml.
[d]The percentage of each disorder group which had LAMP-1 levels above the 95th percentile of the control population (448 ng/ml).
[e]Mucopolysaccharidosis.
[f]Glycosaminoglycan.

EXAMPLE 5

LAMP-1 levels in LSD Patients Following Treatment

Plasma levels of LAMP-1 were determined as described in Example 3, for plasma samples derived from LSD affected patients before and after treatment comprising bone marrow transplantation (for MPS I and MPS VI) or enzyme replacement therapy (for Gaucher disease). The results show that in each case the plasma LAMP-1 levels decrease, to within or close to the normal range, following treatment (Table 2). These data suggest that LAMP-1 may be useful as a marker of the progression and efficacy of therapy.

TABLE 2

LAMP-1 levels in LSD Patients Following Treatment

| Patient Number | Disorder | Age | LAMP-1 Level[a] |
|---|---|---|---|
| 1 | MPS I | 1.8 | 1210 |
| 1 | MPS I | 2.3 | 1135 |
| BMT[b] | | 2.3 | |
| 1 | MPS I | 2.8 | 504 |
| 1 | MPS I | 8.0 | 630 |
| 2 | MPS VI | 1.5 | 1115 |
| 2 | MPS VI | 12.0 | 734 |
| BMT | | 12.0 | |
| 2 | MPS VI | 12.1 | 474 |
| 2 | MPS VI | 12.2 | 457 |
| 3 | Gaucher | 5.8 | 1268 |
| ERT[c] | | 11.5 | |
| 3 | Gaucher | 12.5 | 744 |
| 3 | Gaucher | 12.8 | 602 |
| 3 | Gaucher | 12.9 | 616 |

[a]LAMP-1 level present in plasma (ng/ml)
[b]Bone Marrow Transplant
[c]Enzyme Replacement Therapy

EXAMPLE 6

Levels of Plasma LAMP-1 in Gaucher Affected Siblings

LAMP-1 was determined in the plasma of two Gaucher affected siblings. Both individuals were genotyped to have the same mutations, yet one was asymptomatic at age 7, while the other showed a severe clinically phenotype at age 4. The asymptomatic sibling had a LAMP-1 level of 417 ng/ml (within the normal range), the affected sibling had a LAMP-1 level of 787 ng/ml (above the normal range)

These data suggest that LAMP-1 is a useful indicator of clinical severity and the requirement for therapy and the effectiveness of therapy

EXAMPLE 7

Immunoquantification of LAMP-2

Monoclonal and polyclonal antibodies against LAMP-2 and pure LAMP-2 were supplied by Dr. S. Carlsson. Department of Medical Biochemistry and Biophysics, Umea University, Umea. S-901 87, SWEDEN.

The immunoquantification of LAMP-2 was essentially as described for LAMP-1 except that a secondary, $Eu^{3-}$ labelled, rabbit anti-mouse IgG was used in place of an anti-LAMP-2 monoclonal antibody label directly with $Eu^{3+}$.

Microtitre plates (Immulon 4 Dynatech Laboratories, Inc. Virginia, USA) were coated with anti-LAMP-2 polyclonal antibody at 5 µg/ml for 4 h at 37° C. (100 µL/well diluted in 0.1 M $NaHCO_3$) and washed with DELFIA® wash buffer (×6). Samples were diluted in DELFIA® assay buffer containing 1000 ng/ml of anti-LAMP-2 monoclonal antibody (100 µL/well) and incubated in wells overnight at 4° C. Plates were then washed (×6) and incubated with $Eu^{3+}$ labelled, rabbit anti-mouse IgG DELFIA® for 2 h at 20° C. The plates were washed (×6) and enhancement buffer (200 µL per well) was added, the plates shaken for 10 min at room temperature and the fluorescence measured on a 1234 DELFIA® Research Fluorometer.

LAMP-2 was determined in plasma samples from 14 LSD affected individuals and 4 unaffected individuals. The unaffected individuals had a mean level of 3.1 ug/ml, the levels of the LSD affected individuals ranged from 1.2 to 17.7 ug/ml (FIG. 5). Elevation of LAMP-2 was seen in all disorders were an elevation of LAMP-1 had been observed and in addition, a Pompe affected individual which did not show an elevation of LAMP-1 did show an elevation of LAMP-2. The level of LAMP-2 in plasma was approximately 10-fold higher than the level of LAMP-1 which will enable the easier detection of LAMP-2 in blood samples.

EXAMPLE 8

Sucrosome Formation as a Model of Lysosomal Storage Disorders

Cell Culture

Human diploid fibroblasts were established from skin biopsies submitted to Women's and Children's Hospital, Adelaide, Australia, for diagnosis (Hopwood et al. 1982). Cell lines were maintained according to established procedures in Basal medium Eagle's (BME), 10% (v/v) fetal calf serum (FCS) and antibiotics, in a 5% (v/v) $CO_2$ atmosphere incubator, unless otherwise stated.

Skin fibroblasts were plated in 75 $cm^2$ flasks with BME media and allowed to reach confluence. Once confluent, cells were grown in the BME media containing 100 mM sucrose for 1–35 days to induce sucrosome formation, while control cells remained on BME (no sucrose). LSD affected cell lines were grown under the same conditions, without sucrose. For electron microscopy, fibroblasts were grown in 25 $cm^2$ tissue culture flasks under identical conditions.

Sucrosome containing cells were corrected by the addition of invertase (0.1 mg/ml, Grade VII, ~400 U/mg; Sigma) to the BME culture media or alternatively, the cells were placed on sucrose free BME media. LSD affected cell lines were corrected by the addition of α-glucosidase (50 nmol/min/ml), as described in Fuller et al. (1995), for Pompe disease cells, iduronate-2-sulphatase (50 nmol/min/ml) (Bielicki et al, 1993) for MPS-II or 4-sulphatase (0.5 μg/ml) (Anson et al, 1992) for MPS-VI.

Preparation of Cell Extracts

Cells were washed twice with Dulbecco's phosphate-buffered saline (PBS) and removed from the flask by trypsination (2 ml trypsin-versene solution (CSL Limited, Melbourne, Australia) per flask for 5 min at 37° C.). The cells were immediately washed twice with cold PBS and cells from one flask from each time point were resuspended in 200 μL saline containing 1% (v/v) Nonidet P40. Cell lysates were prepared by 5 cycles of freeze/thaw, clarified by microcentrifugation (1000×g, 5 min) and assayed for lysosomal enzymes and proteins.

Protein/Enzyme Assays

Protein was determined using the bicinchoninic acid method with bovine serum albumin (BSA) as a standard (Smith et al, 1985). The following enzyme activities were determined using fluorogenic substrates. Acid phosphatase activity was determined with 4-methylumbelliferyl-phosphate (Kolodny and Mumford, 1976), β-hexosaminidase with 4-methylumbelliferyl 2-acetamido-2-deoxy-β-D-glucopyranosidase (Leaback and Walker, 1961), α-mannosidase with 4-methylumbelliferyl-α-L-mannopyranoside (Avila and Convit, 1973) and α-iduronidase with 4-methylumbellifervl-α-L-iduronide (Clements et al, 1985). The activity of 4-sulphatase was determined using the immune-capture assay as described by Brooks et al. (1994). α-Ketoglutarate dehydrogenase was measured by a radiochemical assay in which α-$[1-^{14}C]$ ketoglutaric acid was generated in situ from $[1-^{14}C]$ glutamate, as described by Singh et al. (1987). Galactosyl-transferase was measured by a modification of Rome et al.(1979), where $^3$H-UTP-galactose was used in place of $^{14}$C-UTP-galactose. Enzyme activity levels were normalized to total protein content.

Immunoquantification of LAMP-1

Lamp-1 determinations were performed as described in Example 3.

Electron Microscopy

Fibroblast cells were harvested then fixed for 2–3 hours with 2% (v/v) formaldehyde and 2% (v/v) glutaraldehyde in 0.1 M cacodylate buffer containing 5 mM calcium chloride, pH 7.2. Specimens were postfixed in 1% (w/v) osmium tetroxide in 0.1 M cacodylate buffer and 5 mM calcium chloride, pH 7.2. Specimens were dehydrated in a graded series of aqueous ethanol and embedded in Spurr's low viscosity epoxy resin (TAAB, Berkshire, United Kingdom).

Semi-thin (1 μm thick) survey sections were obtained using an Ultracut Ultramicrotome (Leica, Vienna, Austria) and stained with 1% (w/v) toluidine blue in 1% (w/v) borax. For each block a correctly orientated area for sectioning was selected. Ultrathin sections with a silver interference colour (60–90 nm thick) were cut and mounted on 100 mesh hexagonal copper (G 100 HEX) grids (Gilder Grids, Grantham, United Kingdom). Sections were stained with 2% (w/v) uranyl acetate in 50% (v/v) aqueous ethanol followed by Reynolds lead citrate and examined with a Hitachi H-7000 transmission electron microscope (Hitachi, Tokyo. Japan), operating at an accelerating voltage of 75 kV.

Immunofluorescence

After harvesting, cells for immunofluorescence (~$10^5$ cells) were plated and grown for a further 24 hr at 37° C. in tissue culture chamber slides (Nunc) in media plus or minus sucrose or in media containing 0.1 mg/ml invertase as indicated. Cells were then washed twice with PBS and fixed with 1% (v/v) formaldehyde in PBS for 30 min at 4° C., washed twice with methanol and allowed to air-dry. Slides were stored at −20° C. until further processing.

Slides were allowed to come to room temperature, and washed twice with PBS before blocking (3×15 min) with 10% (v/v) FCS in PBS. Slides were incubated for 3 hr at room temperature with the primary antibody (anti-LAMP-1 monoclonal antibody; hybridoma supernatant) containing 0.05% (w/v) digitonin. Slides were then washed three times for 5 min and then incubated for one hour in the dark at 4° C. with the FITC conjugated anti-mouse Ig (Silenus) which had been absorbed against ovalbumin/BSA coupled Affigel (2 mg/ml each). Slides were finally washed three times for 5 min with PBS, coverslips mounted in 50% (v/v) glycerol containing 2% (w/v) DABCO (diazabicyclo[2.2.2.]octane) and examined by epi-fluorescent microscopy.

Results (Lysosomal Biogenesis is Up-Regulated with Sucrosome Formation)

Sucrosomes in skin fibroblasts, were visible by light microscopy within 24 hr of introducing sucrose into the culture media. A series of sucrose concentrations (50 mM. 100 mM, 150 mM, 200 mM, and 250 mM sucrose) were compared for their effect on lysosomal enzyme expression and cell morphology. Skin fibroblasts were grown as contact inhibited, confluent, normal cell monolayers, which enabled them to be studied for many days without passaging. Fibroblasts were incubated in the various sucrose concentrations for 7 days, after which they were harvested and lysosomal enzymes assayed. Cells incubated in 200 mM and 250 mM sucrose-containing media showed signs of osmotic stress after 7 days. A sucrose concentration of 100 mM was found to be optimal in that cells showed no signs of osmotic stress and lysosomal enzyme levels were found to be maximally elevated (results not shown), and 100 mM sucrose in the culture media was routinely used for sucrosome induction.

Time-course experiments were performed in which fibroblasts were incubated in the presence or absence of 100 mM sucrose for 1–28 days. Cells were harvested at 1, 2, 4, 7, 14, 21, and 28 days after being cultured in either sucrose-containing media or normal media. Electron microscopy of cells grown in sucrose containing media, showed a dramatic increase in sucrosomes after only 24 hr, with a further increase in storage during the time-course (FIG. 6, Panels A,B,C,D). Concurrent immunofluorescent labeling of these cells with an anti-LAMP-1 monoclonal antibody, showed an increase in fluorescent labeling associated with lysosomes (FIG. 6, Panels E,F,G,H).

The level of LAMP-1 protein increased 25-fold in the presence of sucrose over a 21 day period (FIG. 7). Immunofluorescent localisation of LAMP-1 in sucrosome containing cells showed that it was present in the sucrosome membrane with no significant elevation at the plasma membrane (FIG. 6. Panels E,F,G,H). The increase in LAMP-1 also correlated with the formation of sucrosomes as determined by electron microscopy revealing not only an increase in size (compare FIGS. 6A and 6B), but also an apparent increase in the number of these lysosomal storage vacuoles (compare FIGS. 6B and 6D), with sucrosomes occupying most of the cytoplasm by days 21–28. However, although the presence of sucrosomes was evident after one day, both by electron microscopy (FIG. 6B) and immunofluorescent labeling (FIG. 6F), no corresponding increase in LAMP-1 was observed at this time (FIG. 7), suggesting an initial increase in sucrosome volume due to swelling, LAMP-1 was not elevated until day 4, with the highest elevation observed at day 21 (FIG. 7), which corresponds with the apparent increase in sucrosome number during this time (FIG. 6D).

Enzyme activity levels of acid phosphatase, β-hexosaminidase, α-iduronidase, α-mannosidase, galactosyltransferase and α-ketoglutarate dehydrogenase during the induction of sucrosomes were investigated. The levels of acid phosphatase, β-hexosaminidase and α-mannosidase within the cells, showed similar profiles to that seen for LAMP-1 but were elevated 3, 4 and 5-fold respectively after 21 days (Table 3). α-Iduronidase, galactosyltransferase (golgi marker) and α-ketoglutarate dehydrogenase (mitochondrial marker) activity levels did not appear to be elevated during lysosomal storage. Protein and enzyme activity levels were also determined in the media (Table 4), where we observed that LAMP-1, β-hexosaminidase, α-mannosidase and 4-sulphatase were secreted from the cells. Whereas LAMP-1, β-hexosaminidase and 4-sulphatase displayed a corresponding increase in the levels secreted when the cells were grown in sucrose containing media, the α-mannosidase showed no such increase. Comparison of the amount of α-mannosidase secreted, with the level present in the cell, indicates that the 5-fold elevation of α-mannosidase activity observed in sucrosome containing cells was not due to an increase in α-mannosidase synthesis but rather an increase in the proportion of α-mannosidase trafficked to the lysosome.

TABLE 3

Protein/Enzyme Levels in Skin Fibroblasts at two weeks post confluency

| Cell line | LAMP-1 | β-Hex[b] | ACP[b] | α-Mann[b] | α-Idu[b] | 4-Sul[b] |
|---|---|---|---|---|---|---|
| normal (n = 4) | 1 | 1 | 1 | 1 | 1 | 1 |
| Pompe | 5 | 2–3 | 1 | 2 | 1 | 2 |
| Salla | 7 | 2–3 | 2 | 2 | 2 | 2 |
| MPS-II | 2 | 2–3 | 2–3 | 2 | 1 | 2 |
| MPS-VI | 1 | 1 | 1 | 1 | 1 | 1 |
| Sucrosome[a] | 25 | 4 | 3 | 5 | 1 | 2 |

[a]level of proteins/enzymes. 3 weeks after cells were placed in sucrose containing media.
[b]β-hexosaminidase (β-Hex), acid phosphatase (ACP), α-mannosidase (α-Mann), α-iduronidase (α-Idu) and 4-sulphatase (4-Sul) activities

TABLE 4

Protein Levels in Sucrosome Containing Cells and Media

| | LAMP-1 [total fluorescence units (×10⁶)] Cell:Media[c] | β-Hex[a] (nmol/min) Cell:Media[c] | α-Mann[a] Cell:Media[c] | 4-Sul[a] Cell:Media[c] |
|---|---|---|---|---|
| Day 14 (S−)[b] | 3:7 | 9:38 | 0.2:67 | 24:86 |
| Day 35 (S−)[b] | 6:7 | 19:24 | 0.6:45 | 18:89 |
| Day 14 (S+)[b] | 14:9 | 34:12 | 1.3:28 | 52:163 |
| Day 21 (S+)[b] | 20:11 | 36:23 | 1.0:35 | 52:307 |
| Day 28 (S+)[b] | 51:22 | 91:113 | 2.4:34 | 63:651 |
| Day 35 (S+)[b] | 58:31 | 114:153 | 3.1:37 | 125:1091 |
| Day 15 (INV)[b] | 8:5 | 55:8 | 1.6:8 | 55:13 |
| Day 18 (INV)[b] | 3:5 | 37:37 | 0.7:45 | 41:126 |
| Day 21 (INV)[b] | 2:7 | 45:49 | 0.6:57 | 49:240 |
| Day 28 (INV)[b] | 1:6 | 57:43 | 0.5:67 | 24:163 |
| Day 35 (INV)[b] | 2:7 | 42:24 | 0.4:51 | 61:179 |
| Day 15 (N)[b] | 13:4 | 27:1 | 0.9:15 | 36:11 |
| Day 18 (N)[b] | 12:10 | 33:8 | 1.0:31 | 48:121 |
| Day 21 (N)[b] | 9:13 | 48:22 | 0.9:31 | 67:265 |
| Day 28 (N)[b] | 4:11 | 28:22 | 0.4:39 | 58:381 |
| Day 35 (N)[b] | 4:8 | 30:21 | 0.3:68 | 70:414 |

[a]β-Hex; β-hexosaminidase; α-Mann, α-mannosidase; 4-Sul, 4-sulphatase.
[b]S−, cells grown in BME media (no sucrose) throughout the time-course; S+, cells grown in BME media containing 100 mM sucrose; INV, cells corrected with 0.1 mg/ml invertase; N, cells corrected by being placed on BME media (no sucrose). Cells were fed by medium change every 7 days.
[c]activities present in media represent total activity secreted since the last median change (i.e. 7 days in all cases except for day 15 and day 18 which were 1 day and 4 days post media change, respectively).

EXAMPLE 9

Sucrosome Dissipation as a Model of the Correction of a Lysosomal Storage Disorder Cell culture methods, preparation of extracts, protein/enzyme assays, immunoquantification of Lamp-1, electron microscopy and immunofluorescence were performed as described in Example 8.

In order to study the effects of storage correction upon lysosomal biogenesis, fibroblasts were incubated in the presence or absence of 100 mM sucrose for 14 days, at that time cells were changed to either normal media; media containing invertase; or continued on sucrose-containing media. Cells that were crown in normal media from day 0 were continued in this media.

Electron microscopy verified that cells grown in sucrose-containing media for 14 days contained sucrosomes (FIGS. 8A & 8B) and sucrosomes continued to accumulate to day 28 (FIG. 6D). The number of sucrosomes were markedly reduced within 24 hr (FIGS. 8C & 8D) of the sucrosome-containing cells being returned to either normal media or to media containing invertase. The cells returned to normal within 4 days (day 18 of the time-course) (FIGS. 8E & 8F).

Sucrosome-containing cells placed on invertase, showed a faster correction with a greater decrease in the number of sucrosomes within 24 hr.

Immunofluorescence studies also showed a decrease in LAMP-1 fluorescent labelling after correction. This labelling was distinctively lysosomal (LAMP-1 positive, MPR negative), with little or no cell surface staining detected. A decrease in LAMP-1 immunofluorescence was observed within 24 hr of cells being transferred to normal media or invertase, with the LAMP-1 labeling observed at this time point, similar to that seen in the cells which were grown continuously on normal media (data not shown).

The level of LAMP-1 protein increased 28-fold in cells grown in the presence of sucrose over a 35 day time-course (FIG. 9). This level returned to normal within 3 days, after sucrosome loaded cells were switched to media containing invertase. However, cells placed on normal media, required 7–14 days to normalise the level of LAMP-1.

Enzyme levels in cells that were grown in sucrose-containing media for 14 days and subsequently placed on normal media required 7 to 14 days to return to normal levels. As with LAMP-1, cells switched to invertase containing media showed the most dramatic change in enzymes levels, with levels decreasing to normal or below normal within 1–4 days. These invertase results correlated strongly with the formation and dissipation of storage vacuoles as observed with electron microscopy and immunofluorescence, whereas the cells placed on normal media showed a lag time between dissipation of vacuoles and decrease in enzyme/protein levels.

During correction of sucrosome containing cells, LAMP-1 and lysosomal enzyme activities were determined in the cells and media (Table 4). This shows that when cells were corrected with invertase, total levels of LAMP-1 decreased from 14 units (in cells prior to correction, day 14 (+ sucrose)) to 13, 8, and 9 units (total in cells plus media, at 15, 18 and 21 days, respectively), but increased over the same period when cells were switched to BME media (no sucrose). In contrast, the total enzyme activity levels increased, during correction with either method.

EXAMPLE 10

Lysosomal Protein/Enzyme Levels in LSD Affected Skin Fibroblasts

Cell culture methods, preparation of extracts, protein/enzyme assays, immunoquantification of Lamp-1, electron microscopy and immunofluorescence were performed as described in Example 8.

Normal skin fibroblast cell lines used in this study, included SF3921, SF4117, SF4153, SF4204 and SF4227. The affected cell lines cultured included SF3960 for Pompe disease, SF1594 for Salla disease, SF1779 for MPS-II and SF3168 for MPS-VI. Cell lines refer to the National Referral Laboratory cell bank held in the Department of Chemical Pathology, Women's and Children's Hospital, Adelaide, Australia.

An elevation in lysosomal enzymes, similar to the increase seen with sucrosome induction, was also observed in LSD patient cell lines. In this study four LSD fibroblast cell lines (Pompe, Salla disease, MPS-II and MPS-VI) and four different normal control fibroblast cell lines were investigated.

Immunofluorescence studies showed a high level of LAMP-1 staining in Pompe cells (FIG. 10A) when compared to normal control fibroblasts (FIG. 6A). Salla, MPS-II and MPS-VI cells showed lower levels of LAMP-1 immunofluorescence, but still greater than the control cells. In all four disease cell lines, this labeling was associated with intracellular organelles (FIG. 10). Electron microscopy verified the presence of a large number of lysosomal storage vacuoles associated with Pompe, Salla and MPS-II cells but relatively few associated with MPS-VI cells (FIG. 11). Immunofluorescence studies with anti-LAMP-1 antibody revealed an increase in staining with time, once the cells reached confluency. Electron microscopy further verified elevated levels of lysosomes in Salla, Pompe and MPS-II cells, when compared to normal fibroblasts, over a 14 day post confluent period (results not shown). MPS-VI cells showed no apparent increase in storage vacuoles over the 14 day incubation.

The Salla disease cells displayed the highest elevation of LAMP-1 protein (7-fold above normal controls) which remained stable over the 14 day time-course. Pompe cells also produced a higher level of LAMP-1 (5-fold above normal) when compared to the level of LAMP-1 in normal fibroblast. A 2-fold increase in LAMP-1 was observed in the MPS-II disease cells throughout the 14 day time-course but no significant elevation was seen in the MPS-VI cells.

Lysosomal enzymes were also elevated in LSD affected cell lines. β-Hexosaminidase was elevated 2–3 fold in the Salla, Pompe, and MPS-II cell lines, when compared to enzyme levels in normal skin fibroblasts (Table 3). α-Mannosidase was also up-regulated up-to 2-fold in Salla, Pompe and MPS-II cells. Acid phosphatase was observed to be increased up-to 2-fold in Salla and MPS-II cells, however no elevation of acid phosphatase was measured in Pompe cells, α-Iduronidase was only found to be elevated (2-fold) in the Salla disease cells, with no increase determined in Pompe, MPS-II, and MPS-VI. Of the four disease cell lines studied, MPS-VI showed no elevation in the levels of the four soluble lysosomal enzymes assayed, when compared to enzyme levels in normal skin fibroblasts (Table 3). No difference in the level of mRNA encoding 4-sulphatase was observed in any of the affected cell lines when compared to the level produced in normal fibroblast cells. However, these affected cell lines were only studied over a 14 day time course, whereas the increase in 4-sulphatase mRNA detected in the sucrosome time-course was not observed until later, at days 21–28. A slight increase (less than 2-fold) was observed in 4-sulphatase activity levels in Salla, Pompe and MPS-II cell lines, similar to the sucrosome time-course (Table 3).

EXAMPLE 11

Lysosomal Protein/Enzyme Levels in LSD Affected Skin Fibroblasts after Correction Cell culture methods, preparation of extracts, protein/enzyme assays, immunoquantification of Lamp-1, electron microscopy and immunofluorescence were performed as described in Example 8.

Correction of the storage in patient cell lines was achieved by the addition of the recombinant enzymes into the culture media of cells. All recombinant enzyme concentrations used have been previously shown to result in the correction of lysosomal storage (Fuller et al, 1995; Bielicki et al. 1993: Anson et al, 1992). Electron microscopy confirmed correction in Pompe and MPS-II affected cells, with the size of storage vacuoles dramatically decreasing within 7 days after the addition of the enzyme. In the case of MPS-VI affected cells, storage was observed to be minimal, with only a few storage vacuoles present, as detected by electron microscopy. Hence no change was observed upon correction. Immunofluorescence studies with anti-LAMP-1 monoclonal antibody also demonstrated a decrease in LAMP-1 staining as a consequence of correction. Pompe affected cells showed intense fluorescent labeling with the LAMP-1 antibody (FIG. 10A), however within 3 days of correction, Pompe cells were normalised, resulting in a decrease in fluorescent labeling (not shown). Correction and subsequent normalization of MPS-II and MPS-VI cells also showed decrease in lysosomal labeling within 7 days.

As a result of Pompe and MPS-II correction, the elevated LAMP-1 protein levels were observed to decrease to the level of normal controls within 3–7 days (FIG. 12). The activity levels of the lysosomal enzymes acid phosphatase. β-hexosaminidase, α-iduronidase and α-mannosidase, were all elevated 2–3 fold in the MPS-II and Pompe disease cells, when compared to normal fibroblast levels. Correction of MPS-II with iduronate-2-sulphatase, resulted in these lysosomal enzymes returning to the normal range within 7 days of correction. Surprisingly no significant change in the elevated lysosomal activity levels was observed with the correction of the Pompe disease cells, although a decrease in storage vacuoles was detected with electron microscopy and immunofluorescence studies, as well as an accompanying decrease in the LAMP-1 levels. MPS-VI disease cells did not display elevated levels in any of the lysosomal enzymes assayed and no increase in LAMP-1 normally observed with other storage disorders (results not shown). Thus, only a small difference existed between affected and corrected cells and no significant change was detected as a result of correction.

REFERENCES

1. Anson, D. S., Taylor, J. A., Bielicki. J., Harper, G. S., Peters, C., Gibson, G. J., and Hopwood, J. J. (1992) Correction of human mucopolysaccharidosis type VI fibroblasts with recombinant N-acetylgalactosamine-4-sulphatase. Biochem. J. 284, 789–794.
2. Avila, J. L. and Convit, J. (1973) Characterisation and properties of a-D-mannosidase of human polymorphonuclear leucocytes, Clin. Chim. Acta 51, 335–343.
3. Bielicki. J., Hopwood. J. J., Wilson. P. J., and Anson. D. S. (1993) Recombinant human iduronate-2-sulphatase: correction of mucopolysaccharidosis-type II fibroblasts and characterization of the purified enzyme. Biochiem. J. 289, 241–246.
4. Brooks. D. A., Gibson, G. J., and Hopwood. J. J. (1994) Immunochemical characterization of feline and human N-acetylgalactosamine 4-sulfatase. Biochem. Med. Met. Biol. 53, 58–66.
5. Bullock et al. (1982, 1983, 1984) Techniques in Immunocytochemistry Academic Press, Orlando.
6. Chard. (1986) In: An Introduction to radio immunoassay and related techniques. Elsevier Science, Amsterdam, The Netherlands.
7. Clements. P. R., Brooks, D. A., Saccone, G. T. P., and Hopwood J. J. (1985) Human α-L-iduronidase. 1. Purification, monoclonal antibody production, native and subunit molecular mass. Eur. J. Biochem. 152, 21–28.
8. Cole et al. (1985) In: Monoclonal antibodies in cancer therapy, Alan R. Bliss Inc. pp 77–96.
9. Crawley A. C. et al. Enzyme replacement therapy in a feline model of Maroteaux-Lamy syndrome. J. Clin. Invest. 1996; 97:1864–1873.
10. Crawley A. C. Neidzielski K. H., Issac E. L., Davey R. C. A., Byers, S., Hopwood, J. J. Enzyme replacement therapy from birth in a feline model of mucopolysaccharidosis type VI.J. Clin. Invest. 1997; 99:651–662.
11. Dahlgren, C., Carlsson, S. R., Karlsson, A., Lundqvist, H., and Sjölin, C. (1995) The lysosomal membrane glycoproteins LAMP-1 and LAMP-2 are present inmobilizable organelles, but are absent from the azurophil granules of human neutrophils, Biochem. J. 311, 667–674.
12. Diamandis, E. P. Immunoassays with time-resolved fluorescence spectroscopy: principles and applications. Clin. Biochem. 1988; 21:139–150.
13. Fuller, M., van der Ploeg, A., Reuser, A. J. J., Anson, D. S., and Hopwood, J. J. (1995) Isolation and characterisation of a recombinant, precursor form of lysosomal acid α-glucosidase. Euro. J. Biochem. 234, 903–909.
14. Gahl, W. A., et al. Cysteamine therapy for children with nephropathic cystinosis. N. Engl. J. Med. 1987; 316:971–977.
15. Haskins, M. E., Otis, E. J., Hayden, J. E., Jezyk, P. F., Stramm, L. Hepatic storage of glycosaminoglycans in feline and canine models of mucopolysaccharidoses I, VI and VII. Vet. Pathol. 1992; 29:112–119.
16. Hemmila, I., Lanthanides as probes for time-resolved fluorometric immunoassays. Scand. J. Clin. Lab. Invest. 1988; 48:389–399.
17. Hoogerbrugge, P. M., et al. Allogenic bone marrow transplantation for lysosomal storage diseases. The European Group for Bone Marrow Transplantation [see comments]. Lancet 1995; 245:1398–1402.
18. Hopwood, Muller, V., Harrison, J. R., Carey, W. F., Elliott, H., Robertson. E. F. and Pollard, A. C. (1982) Enzymatic diagnosis of the mucopolysaccharidoses. Med. J. Aust, 1982; 1:257–260.
19. Hopwood, J. J., et al. Long-term clinical progress in bone marrow transplanted mucopolysaccharidosis type I patients with a defined genotype. J. Inherit. Metab. Dis. 1993; 16:1024–1033.
20. Huse et al. (1989) Science 246: 1275–1281.
21. Jones, M. Z., Kennedy, F. F., Caprine beta-mannosidosis: aberrat phenotype in a 5-month-old euthyroid animal. J. Inherit. Metab. Dis. 1993; 16:910–911.
22. Kampine, J. P., Brady, R. O., Kanfer, J. N., Feld M., Shapior, D. Diagnosis of Gaucher disease and Niemass-Pick disease with small samples of venous blood. Science 1967; 155:86–88.
23. Kohler and Milstein (1975) Nature, 256: 495–499.
24. Kozbor et al. (1983) Immunol. Today 4: 72;
25. Kolodny, E. H., and Mumford, R. A. (1976) Human leukocyte acid hydrolases: Characterisation of eleven lysosomal enzymes and study of reaction conditions for their automated analysis. Clin. Chim. Acta. 70, 247–257.
26. Leaback, D. H. and Walker, P. G. (1961) Studies on glucosaminidase. IV. The fluorometric assay of N-acetyl-β-glucosaminidase. Biochem. J. 78, 151–156.
27. Markello, T. C., Bernardini, I. M., Gahl, W. A. Improved renal function in children with cystinosis treated with cysteamine. N. Engl. J. Med. 1993; 328:1157–1162.
28. Meikle, P. J., Whittle, A. M., Hopwood. J. J. Human acetyl-coenzyme A:alpha-glucosaminide N-acetyltransferase. Kinetic characterisation and mechanistic interprctation. Biochem. J. 1995; 308:327–333.
29. Neufeld, E. F., Meunzer, J. The Mucopolysaccaridosis. In Scriver, C. R., Beaudet, A. C., Sly, W. S., Valle, D., eds. The Metabolic and Molecular Basis of Inherited Disease (Seventh Edition). New York: McGraw-Hill Inc. 1995: Vol II, 2465–2494.
30. Otterbach, B., Stoffel, W. Acid sphingomyelinase-deficient mice mimic the neurovisceral form of human lysosomal storage disease (Niemann-Pick disease). Cell 1995; 81:1053–1061.

31. Rome, L. H., Garvin. A. J., Allietta, M. M. and Neufeld, E. F. (1979). Two species of lysosomal organelles in cultured human fibroblasts. *Cell* 17, 143–153.
32. Sands, M. S. et al. Enzyme replacement therapy for murine mucopolysaccharidosis type VII J. Clin. Invest. 1994; 93:2324–2331.
33. Singh, H, Derwas, N. and Poulos, A. (1987). Very long chain fatty acid beta-oxidation by subcellular fractions of normal and Zellweger syndrome skin fibroblasts. *Arch Biochem Biophys* 257, 302–314.
34. Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) Measurement of protein using bicinchoninic acid. Anal. Biochem. 150, 76–85.
35. Taylor, R. M., Stewart, G. J., Farrow, B. R. Improvement in the neurologic signs and storage lesions of fucosidosis in dogs given marrow transplants at an early age. Transplant, Proc. 1989; 21:3818–3819.
36. Thompson, J. N., Jones, M. Z., Dawson, G., Huffman, P. S. N-acetylglucosamine 6-sulphatase deficiency in a Nubian goat: a model of Sanfilippo syndrome type D (mucopolysaccharidosis IIID)1. J. Inherit, Metab. Dis. 1992; 15:760–768.
37. Tijssen (1985) Practice and Theory of enzyme immunoassays: Laboratory Techniques in Biochemistry and Molecular Biology, Elsevier Science, Amsterdam, The Netherlands.
38. Zhou, X. Y. et al. Mouse model for the lysosomal disorder galactosialidosis and correction of the phenotype with overexpressing erythroid precursor cells. Genes Dev. 1995; 9:2623–2634.
39. Zola, H. and Brooks, D. Techniques for the Production and characterization of Monoclonal Hybridoma Antibodies. In Hurrell J. G. R., ed. Monoclonal Hybridoma Antibodies: Techniques and Application. Boca Raton: CRC Press, Inc. 1982: 1–57.

The claims defining the invention are as follows:

1. A method of detecting a lysosomal storage disorder (LSD), monitoring the progress of a LSD or the efficacy of treatment of a LSD in a human or animal subject, the method comprising assaying the level of Lamp-1 (lysosome-associated membrane protein type-1) in a biological sample derived from the subject, wherein
   the biological sample is a blood, serum, plasma or urine sample; and
   an increase in the level of Lamp-1 in the subject relative to the corresponding level of Lamp-1 in a non-affected individual or population is indicative of a LSD.
2. The method according to claim 1, wherein the biological sample is a blood, plasma or urine sample.
3. The method according to claim 1, wherein the biological sample is a blood, plasma, or serum sample.
4. The method according to claim 2, wherein the biological sample is a blood sample.
5. The method according to claim 2, wherein the biological sample is a urine sample.
6. The method according to claim 1, wherein the LSD is selected from the list set forth in Table 1.
7. The method according to claim 6, wherein the LSD is selected from the group consisting of MPS I, MPS II, Gaucher disease, Pompe disease and Salla's disease.
8. The method according to claim 1, wherein the step of assaying the level of Lamp-1 comprises measuring the enzyme activity of Lamp-1 in the biological sample.
9. The method according to claim 1, wherein the step of assaying the level of Lamp-1 comprises contacting the biological sample with one or more antibodies specific for Lamp-1 for a time and under conditions sufficient for the formation of a complex to occur.
10. The method according to claim 9, wherein the one or more antibodies are monoclonal antibodies.
11. The method according to claim 9, wherein the one or more antibodies is/are labeled with a reporter molecule.
12. The method according to claim 9, further comprising the step of contacting the complex formed between Lamp-1 and one of the one or more antibodies with a labeled antibody for a time and under conditions sufficient for binding to occur.
13. The method according to claim 12, wherein the labeled antibody is labeled with a reporter molecule.
14. The method according to claim 13, wherein the reporter molecule is an enzyme, a fluorophore or a radionuclide molecule.
15. The method according to claim 14, wherein the enzyme, fluorophore or radionuclide molecule is selected from the group consisting of horseradish peroxidase, glucose oxidase, β-galactosidase, alkaline phosphatase, fluorescein, $EU^{3+}$ and other lanthanide metals, and rhodamine.
16. The method according to claim 1, wherein
   (a) the LSD is selected from the list set forth in Table 1;
   (b) the subject is a human; and
   (c) the biological sample is a human blood, plasma or urine sample.
17. A method for detecting a lysosomal storage disorder (LSD), comprising assaying LAMP-1 (lysosome-associated membrane protein type-1) in a sample of blood obtained from a patient that is asymptomatic for a LSD, an increase in the level of LAMP-1 in the patient relative to the corresponding level of LAMP-1 in a non-affected individual or population being indicative of a LSD.
18. A method of detecting a lysosomal storage disorder (LSD), monitoring the progress of a LSD or the efficacy of treatment of a LSD in a human or animal subject, the method comprising assaying the level of Lamp-1 in a biological sample derived from the subject, wherein:
   the LSD is selected from the group consisting of Galactosialidosis, Gaucher disease, CM1-gangliosidosis, α-Mannosidosis, Mucopolysaccharidosis (MPS) 1, MPS II, MPS IIIA, MPS IIIB, MPS IIIC, MPS IIID, MPS IVA, MPS VI, Multiple sulphatase deficiency, Sandhoff disease, Sialic Acid Storage disease, Tay-Sachs disease, Wolman disease and Salla's disease; and
   an increase in the level of Lamp-1 in the subject relative to the corresponding level of the LSD marker in a non-affected individual or population is indicative of a LSD.
19. The method of claim 18, wherein the LSD is selected from the group consisting of MPS I, MPS II, Gaucher disease, Pompe disease, and Salla's disease.
20. The method according to claim 18, wherein the biological sample comprises blood, plasma, serum, urine, a fibroblast cell, a fibroblast cell culture or a fibroblast cellular extract.
21. The method according to claim 20, wherein the fibroblast cell, fibroblast cell culture or fibroblast cellular extract is a Pompe, Salla, MPS II or MPS VI fibroblast cell, cell culture or cellular extract.
22. The method according to claim 20, wherein the biological sample is a blood, plasma, serum or urine sample.
23. The method according to claim 18, wherein the subject is a human.

24. A method of detecting a lysosomal storage disorder (LSD), monitoring the progress of a LSD or the efficacy of treatment of a LSD in a human or animal subject, the method comprising assaying the level of Lamp-2 (lysosome-associated membrane protein type-2) in a biological sample derived from the subject, wherein the LSD is selected from the group consisting of Pompe disease, Gaucher disease and a Mucopolysaccharidosis (MPS) disease; and an increase in the level of Lamp-2 in the subject relative to the corresponding level of Lamp-2 in a non-affected individual or population is indicative of a LSD.

25. The method of claim 24, wherein the LSD is Gaucher disease or MPS I.

26. The method of claim 24, wherein the biological sample comprises blood, plasma, serum, urine, a fibroblast cell, a fibroblast cell culture or a fibroblast cellular extract.

27. The method according to claim 26, wherein the biological sample is a blood, plasma, serum or urine sample.

28. The method according to claim 24, wherein the subject is a human and the biological sample is a human blood, plasma, serum or urine sample.

* * * * *